United States Patent
Bernhardt et al.

(10) Patent No.: US 9,688,944 B2
(45) Date of Patent: *Jun. 27, 2017

(54) SYNERGISTIC SURFACTANT BLENDS

(71) Applicant: Stepan Company, Northfield, IL (US)

(72) Inventors: Randal J. Bernhardt, Antioch, IL (US); Xue Min Dong, Lincolnshire, IL (US)

(73) Assignee: Stepan Company, Northfield, IL (US)

(*) Notice: Subject to any disclaimer, the term of this patent is extended or adjusted under 35 U.S.C. 154(b) by 147 days.

This patent is subject to a terminal disclaimer.

(21) Appl. No.: 14/395,082

(22) PCT Filed: Apr. 12, 2013

(86) PCT No.: PCT/US2013/036460
§ 371 (c)(1),
(2) Date: Oct. 17, 2014

(87) PCT Pub. No.: WO2013/162924
PCT Pub. Date: Oct. 31, 2013

(65) Prior Publication Data
US 2015/0094383 A1 Apr. 2, 2015

Related U.S. Application Data

(60) Provisional application No. 61/637,599, filed on Apr. 24, 2012.

(51) Int. Cl.
| | | |
|---|---|---|
| *C11D 1/65* | (2006.01) |
| *A01N 25/04* | (2006.01) |
| *A61K 8/46* | (2006.01) |
| *A61K 8/49* | (2006.01) |
| *A61Q 19/00* | (2006.01) |
| *C09K 8/584* | (2006.01) |
| *A61K 8/41* | (2006.01) |
| *A61Q 5/02* | (2006.01) |
| *A61Q 19/10* | (2006.01) |
| *C11D 1/02* | (2006.01) |
| *C11D 1/62* | (2006.01) |

(52) U.S. Cl.
CPC ............ *C11D 1/65* (2013.01); *A01N 25/04* (2013.01); *A61K 8/416* (2013.01); *A61K 8/466* (2013.01); *A61K 8/4946* (2013.01); *A61Q 5/02* (2013.01); *A61Q 19/00* (2013.01); *A61Q 19/10* (2013.01); *C09K 8/584* (2013.01); *A61K 2800/596* (2013.01); *C11D 1/02* (2013.01); *C11D 1/62* (2013.01); *C11D 1/652* (2013.01)

(58) Field of Classification Search
CPC ............ C11D 1/65; C11D 1/652; C11D 1/653
See application file for complete search history.

(56) References Cited

U.S. PATENT DOCUMENTS

| | | |
|---|---|---|
| 2,653,970 A | 9/1953 | Fessler |
| 2,865,968 A | 12/1958 | Hansley et al. |
| 3,155,591 A | 11/1964 | Hllfer |
| 3,169,142 A | 2/1965 | Knaggs et al. |
| 3,193,586 A | 7/1965 | Rittmeister |
| 3,494,924 A | 2/1970 | Bonetti et al. |
| 3,497,555 A | 2/1970 | Dudzinski |
| 3,919,678 A | 11/1975 | Penfold |
| 3,929,678 A | 12/1975 | Laughlin et al. |
| 3,959,461 A | 5/1976 | Bailey et al. |
| 4,087,457 A | 5/1978 | Convers et al. |
| 4,148,821 A | 4/1979 | Nussbaum et al. |
| 4,275,013 A | 6/1981 | Tokosh et al. |
| 4,275,055 A | 6/1981 | Nachtigal et al. |
| 4,285,841 A | 8/1981 | Barrat et al. |
| 4,387,090 A | 6/1983 | Bolich |
| 4,409,399 A | 10/1983 | Swift et al. |
| 4,545,941 A | 10/1985 | Rosenburg |

(Continued)

FOREIGN PATENT DOCUMENTS

| | | |
|---|---|---|
| WO | 2008048522 | 4/2008 |
| WO | 2008081158 | 7/2008 |
| WO | 2011072232 | 6/2011 |
| WO | 2012061092 | 5/2012 |
| WO | 2012061093 | 5/2012 |
| WO | 2012061094 | 5/2012 |
| WO | 2012061095 | 5/2012 |
| WO | 2012061098 | 5/2012 |
| WO | 2012061101 | 5/2012 |
| WO | 2012061103 | 5/2012 |
| WO | 2012061106 | 5/2012 |
| WO | 2012061108 | 5/2012 |
| WO | 2012061110 | 5/2012 |

OTHER PUBLICATIONS

Bergstrom. Langmuir 2001, 17, 993-998.*
G. Djigoue et al., Appl. Catal. A 346 (2009) 158.
J.C. Mol., Green Chem. 4 (2002) 5.
J.C. Mol., Topics in Catal. 27 (2004) 97.
R. Larock, Comprehensive Organic Transformations, pp. 432-434.
M. Smith et al., March's Organic Chemistry, 5th ed. pp. 1541, 1549, 1550.

*Primary Examiner* — Michael A Salvitti
(74) *Attorney, Agent, or Firm* — Dilworth IP LLC

(57) ABSTRACT

Synergistic surfactant blends are disclosed. In one aspect, the blend comprises an anionic surfactant and a metathesis-based cationic surfactant comprising a quaternized derivative. The quaternized derivative is a quaternized fatty amine, quaternized fatty amidoamine, imidazoline quat, or esteramine quat made from a metathesis-derived C10-C17 monounsaturated acid or its ester derivative. Also disclosed are synergistic surfactant blends comprising a cationic surfactant and a metathesisbased anionic surfactant comprising a sulfonated derivative. The sulfonated derivative is a fatty ester sulfonate, fatty acid sulfonate, sulfoestolide, fatty amide sulfonate, sulfonated fatty ester alkoxylate, imidazoline quat sulfonate, sulfonated amidoamine oxide, or sulfonated amidoamine betaine. The synergistic blends have a negative value or a reduced interfacial tension (IFT) when compared with an expected IFT value calculated from the individual surfactant components. Blends of the invention also exhibit surprisingly favorable solubility profiles.

18 Claims, No Drawings

(56) References Cited

U.S. PATENT DOCUMENTS

| | | | | |
|---|---|---|---|---|
| 4,594,455 | A | 6/1986 | Dudzinski | |
| 4,931,216 | A * | 6/1990 | Igarashi | A61K 8/416 424/70.13 |
| 4,994,662 | A | 2/1991 | Funahashi et al. | |
| 5,124,491 | A | 6/1992 | Fleckenstein et al. | |
| 5,143,885 | A | 9/1992 | Warwel et al. | |
| 5,183,791 | A | 2/1993 | Warwel et al. | |
| 5,360,571 | A | 11/1994 | Kilgour et al. | |
| 5,441,541 | A | 8/1995 | Mehreteab et al. | |
| 5,472,455 | A | 12/1995 | Mehreteab et al. | |
| 5,696,294 | A | 12/1997 | Abe et al. | |
| 5,750,492 | A | 5/1998 | Contet et al. | |
| 5,783,534 | A | 7/1998 | Wahle et al. | |
| 5,817,844 | A | 10/1998 | Hama et al. | |
| 5,910,472 | A | 6/1999 | Elliott et al. | |
| 5,939,059 | A | 8/1999 | Franklin et al. | |
| 6,004,913 | A | 12/1999 | Iacobucci | |
| 6,184,400 | B1 | 2/2001 | Hama et al. | |
| 6,306,805 | B1 * | 10/2001 | Bratescu | A61K 8/40 510/119 |
| 6,504,061 | B1 | 1/2003 | Okamoto | |
| 6,528,070 | B1 | 3/2003 | Bratescu | |
| 6,566,313 | B1 * | 5/2003 | Hohenstein | A61K 8/42 510/125 |
| 6,683,224 | B1 | 1/2004 | Hourticolon | |
| 7,208,643 | B2 | 4/2007 | Namba et al. | |
| 7,666,828 | B2 | 2/2010 | Bernhardt et al. | |
| 7,718,816 | B2 * | 5/2010 | Yajima | A61K 8/42 554/35 |
| 7,879,790 | B2 | 2/2011 | Bernhardt | |
| 8,481,747 | B2 | 7/2013 | Schrodi | |
| 8,501,973 | B2 | 8/2013 | Schrodi | |
| 8,569,560 | B2 | 10/2013 | Schrodi | |
| 8,735,640 | B2 | 5/2014 | Cohen | |
| 9,249,373 | B2 * | 2/2016 | Allen | A61K 8/416 |
| 9,249,374 | B2 * | 2/2016 | Allen | A01N 25/04 |
| 9,321,985 | B1 * | 4/2016 | Allen | C11D 1/72 |
| 2001/0006981 | A1 | 7/2001 | Odds et al. | |
| 2003/0190302 | A1 * | 10/2003 | Frantz | A61K 8/0237 424/70.24 |
| 2004/0213905 | A1 | 10/2004 | Breen et al. | |
| 2005/0164903 | A1 * | 7/2005 | Ko | C11D 1/86 510/504 |
| 2005/0236300 | A1 | 10/2005 | Twu et al. | |
| 2006/0157088 | A1 * | 7/2006 | Carter | C11D 1/65 134/42 |
| 2007/0167332 | A1 | 7/2007 | Subramanian et al. | |
| 2009/0188055 | A1 | 7/2009 | Bernhardt et al. | |
| 2009/0264672 | A1 | 10/2009 | Abraham et al. | |
| 2010/0016198 | A1 | 1/2010 | Bernhardt et al. | |
| 2010/0145086 | A1 | 6/2010 | Schrodi et al. | |
| 2010/0282467 | A1 | 11/2010 | Hutchison et al. | |
| 2011/0113679 | A1 | 5/2011 | Cohen et al. | |
| 2011/0230354 | A1 * | 9/2011 | Zhu | A01N 25/30 504/358 |
| 2013/0217608 | A1 * | 8/2013 | Allen | C11D 1/72 510/296 |
| 2013/0225408 | A1 * | 8/2013 | Allen | C11D 1/75 504/206 |
| 2013/0225409 | A1 * | 8/2013 | Allen | C07C 309/69 504/206 |
| 2013/0288946 | A1 * | 10/2013 | Allen | A01N 25/04 510/416 |
| 2014/0080748 | A1 * | 3/2014 | Price | C11D 1/37 510/228 |
| 2014/0336398 | A1 | 11/2014 | Cohen et al. | |
| 2014/0336399 | A1 | 11/2014 | Cohen et al. | |
| 2015/0094383 | A1 * | 4/2015 | Bernhardt | C11D 1/65 514/785 |
| 2016/0102272 | A1 * | 4/2016 | Allen | C11D 1/72 510/298 |

* cited by examiner

SYNERGISTIC SURFACTANT BLENDS

FIELD OF THE INVENTION

The invention relates to blends of cationic and anionic surfactants, and more particularly to blends that exhibit synergy and have favorable solubility profiles.

BACKGROUND OF THE INVENTION

Surfactants and blends of surfactants are important components of laundry detergents, dish detergents, household or industrial cleaners, personal care products, agricultural products, building materials, oil recovery compositions, emulsion polymers, and other products. Blends of surfactants are used frequently to achieve performance characteristics that are not easy to accomplish with a single surfactant type. For example, blends of anionic with nonionic or amphoteric surfactants are commonly used to formulate two-in-one shampoo and conditioner formulations for hair care.

When two surfactants used together provide unexpected surface characteristics compared with what could have been predicted based on summing their individual contributions, the combination exhibits synergy. Synergistic surfactant blends offer economic advantages because the benefits of each component can be realized at lower concentrations. Synergism has been quantified in mathematical terms. See, for example, the background discussion of U.S. Pat. No. 5,360,571, which explains the relationship between critical micelle concentration and $\beta^m$, the mixed micelle parameter. As the reference explains, negative $\beta$ values correspond to synergism, and more negative values indicate greater synergy.

Synergy can also be identified by measuring interfacial tension (IFT) as a function of surfactant blend composition. Minima in such plots correspond to blends having the highest synergy level. See, for example, U.S. Pat. No. 5,441,541 or 5,472,455, particularly Example 2 and FIG. 6. The '541 patent teaches that blends of certain cationic and anionic surfactants exhibit synergism, and the effect is maximized when equimolar amounts of the surfactants are used. According to the patentees, the "strong synergism in surface tension reduction effectiveness and efficiency implies the formation of a new active moiety" ('541 patent at Ex. 2).

Strong synergy has been observed in blends of cationic and anionic surfactants. However, the ability to form complexes and achieve a synergistic effect has tradeoffs, particularly with regard to solubility. Blends of cationic and anionic surfactants are often avoided because the complexes tend to precipitate, especially when the blends are diluted with water. According to U.S. Pat. No. 6,306,805, "most anionic-cationic surfactant mixtures studied are insoluble or only slightly soluble in water . . . At present, very few anionic-cationic surfactant mixtures have been found which produce clear solution phases over a wide concentration range at equimolar composition" ('805 patent at col. 3, ll. 3-13). The reference acknowledges the high probability of synergism in mixtures of anionic and cationic surfactants, but qualifies its value: "However . . . the variations in surfactant type and size that produce progressively more negative $\beta$ values unfortunately are accompanied by decreasing solubility. Hence, anionic-cationic synergism is limited by the formation of an insoluble salt, which typically occurs when the combined number of carbon atoms in the chains of both surfactants totals more than about twenty" ('805 patent at col. 3, ll. 20-43). To overcome the solubility issue, the patentees use a ternary blend that includes a semi-polar nonionic, ethoxylated alkanolamide, or amphoteric/zwitterionic component as a "bridging surfactant."

Improvements in metathesis catalysts (see J.C. Mol, *Green Chem.* 4 (2002) 5) have enabled the manufacture of reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. We recently described how to synthesize a variety of valuable anionic and cationic surfactants from metathesis-based, monounsaturated feedstocks (see, e.g., copending PCT Int. Appl. Nos. US11/57595, US11/57596, US11/57597, US11/57602, US11/57605, and US11/57609, all filed 25 Oct. 2011). Among the cationic surfactants, for instance, we described quaternized fatty amines and quaternized fatty amidoamines made from metathesis-derived $C_{10}$-$C_{17}$ monounsaturated acids and their ester derivatives. Among the anionic surfactants, we described sulfonated esters, sulfoestolides, and fatty amide sulfonates made from metathesis-derived $C_{10}$-$C_{17}$ monounsaturated acids, octadecene-1,18-dioic acid, or their ester derivatives.

Given the tendency of combinations of anionic and cationic surfactants to precipitate from aqueous solutions, particularly when their combined carbon number exceeds twenty, it was unclear whether surfactants made from monounsaturated, metathesis-based feedstocks (with typical carbon numbers 10-18 for one portion of the complex) would offer any advantage for cationic-anionic surfactant blends, even if the blends happened to demonstrate synergy. However, the potential benefits of synergy invited us to explore this possibility.

In sum, the surfactant industry would benefit from the availability of new cationic-anionic surfactant blends, particularly blends that exhibit synergy and could be used to improve the performance and/or economics of end-use applications. Valuable blends would take advantage of the now-available, metathesis-based feedstocks based on soybean oil, palm oil, or other renewable resources. Ideally, the blends would avoid the solubility issues that have, until now, limited their applicability.

SUMMARY OF THE INVENTION

In one aspect, the invention relates to a synergistic surfactant blend comprising a metathesis-based cationic surfactant. The blend comprises: (a) an anionic surfactant; and (b) a cationic surfactant comprising a quaternized derivative. The quaternized derivative is a quaternized fatty amine, quaternized fatty amidoamine, imidazoline quat, or esteramine quat. The quaternized derivative is made from a metathesis-derived $C_{10}$-$C_{17}$ monounsaturated acid or its ester derivative. The blend exhibits synergy as evidenced by a negative $\beta$ value or a reduced interfacial tension (IFT) when compared with an expected IFT value calculated from the individual surfactant components.

In another aspect, the invention relates to a synergistic surfactant blend comprising a metathesis-based anionic surfactant. This blend comprises: (a) a cationic surfactant; and (b) an anionic surfactant comprising a sulfonated derivative. The sulfonated derivative is a fatty ester sulfonate, fatty acid sulfonate, sulfoestolide, fatty amide sulfonate, sulfonated fatty ester alkoxylate, imidazoline quat sulfonate, sulfonated amidoamine oxide, or sulfonated amidoamine betaine. The sulfonated derivative is made from a metathesis-derived $C_{10}$-$C_{17}$ monounsaturated acid, octadecene-1,18-dioic acid, or their ester derivatives. The blend exhibits synergy based on the negative β or IFT comparisons as noted above.

In addition to the negative β or reduced IFT values, blends of the invention exhibit surprisingly favorable solubility profiles. The surfactant blends should be valuable for a wide range of applications, including (among others) laundry detergents, dish detergents, household or industrial cleaners, personal care products, agricultural products, building materials, oil recovery compositions, and emulsion polymers.

DETAILED DESCRIPTION OF THE INVENTION

I. Synergistic Surfactant Blend: Metathesis-Based Cationic Surfactant

One synergistic surfactant blend of the invention comprises a metathesis-based cationic surfactant. The blend comprises an anionic surfactant and a cationic surfactant comprising a quaternized derivative. The quaternized derivative is a quaternized fatty amine, quaternized fatty amidoamine, imidazoline quat, or esteramine quat. The quaternized derivative is made from a metathesis-derived $C_{10}$-$C_{17}$ monounsaturated acid or its ester derivative.

As used herein, "monounsaturated" refers to compositions that comprise principally species having a single carbon-carbon double bond but may also include a minor proportion of one or more species that have two or more carbon-carbon double bonds. The skilled person will appreciate that it is not necessary and often impractical to produce a purely "monounsaturated" species, and that mixtures comprising principally (but not exclusively) monounsaturated acids, esters, and derivatives are contemplated as within the scope of the invention.

A. The Anionic Surfactant

Suitable anionic surfactants are well known in the art. They include, for example, alkyl sulfates, alkyl ether sulfates, olefin sulfonates, α-sulfonated alkyl esters (particularly α-sulfonated methyl esters), α-sulfonated alkyl carboxylates, alkyl aryl sulfonates, sulfoacetates, sulfosuccinates, isethionates, taurates, alkane sulfonates, and alkylphenol alkoxylate sulfates, and the like, and mixtures thereof.

In particular, anionic surfactants useful herein include those disclosed in *McCutcheon's Detergents & Emulsifiers* (M.C. Publishing, N. American Ed., 1993); Schwartz et al., *Surface Active Agents, Their Chemistry and Technology* (New York: Interscience, 1949); and in U.S. Pat. Nos. 4,285,841 and 3,919,678, the teachings of which are incorporated herein by reference.

Suitable anionic surfactants include salts (e.g., sodium, potassium, ammonium, and substituted ammonium salts such as mono-, di-, and triethanolamine salts) of anionic sulfate, sulfonate, carboxylate and sarcosinate surfactants. Other suitable anionic surfactants include isethionates (e.g., acyl isethionates), N-acyl taurates, fatty amides of methyl tauride, alkyl succinates, glutamates, sulfoacetates, and sulfosuccinates, monoesters of sulfosuccinate (especially saturated and unsaturated $C_{12}$-$C_{18}$ monoesters), diesters of sulfosuccinate (especially saturated and unsaturated $C_6$-$C_{14}$ diesters), and N-acyl sarcosinates. Resin acids and hydrogenated resin acids are also suitable, such as rosin, hydrogenated rosin, and resin acids and hydrogenated resin acids present in or derived from tallow oil.

Suitable anionic surfactants include linear and branched primary and secondary alkyl sulfates, alkyl ethoxysulfates, fatty oleyl glycerol sulfates, alkyl phenol ethoxylate sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside. Preferred alkyl sulfates include $C_8$-$C_{22}$, more preferably $C_8$-$C_{16}$, alkyl sulfates. Preferred alkyl ethoxysulfates are $C_8$-$C_{22}$, more preferably $C_8$-$C_{16}$, alkyl sulfates that have been ethoxylated with from 0.5 to 30, more preferably from 1 to 30, moles of ethylene oxide per molecule.

Other suitable anionic surfactants include salts of $C_5$-$C_{20}$ linear alkylbenzene sulfonates, alkyl ester sulfonates, $C_6$-$C_{22}$ primary or secondary alkane sulfonates, $C_6$-$C_{24}$ olefin sulfonates, alkyl glycerol sulfonates, fatty acyl glycerol sulfonates, fatty oleyl glycerol sulfonates, and any mixtures thereof.

Suitable anionic surfactants include $C_8$-$C_{22}$, preferably $C_8$-$C_{18}$, alkyl sulfonates and $C_8$-$C_{22}$, preferably $C_{12}$-$C_{18}$, α-olefin sulfonates. Suitable anionic carboxylate surfactants include alkyl ethoxy carboxylates, alkyl polyethoxy polycarboxylate surfactants and soaps ("alkyl carboxyls"). Preferred sulfosuccinates are $C_8$-$C_{22}$ sulfosuccinates, preferably mono-$C_{10}$-$C_{16}$ alkyl sulfosuccinates such as disodium laureth sulfosuccinate.

Suitable anionic surfactants include sarcosinates of the formula RCON($R_1$)$CH_2$COOM, wherein R is a $C_5$-$C_{22}$ linear or branched alkyl or alkenyl group, $R_1$ is $C_1$-$C_4$ alkyl and M is an ion. Preferred sarcosinates include myristyl and oleoyl methyl sarcosinates as sodium salts. Most preferably, the sarcosinate is a $C_{10}$-$C_{16}$ sarcosinate.

Suitable anionic surfactants include alkyl sulfoacetates of the formula RO(CO)$CH_2SO_3$M, wherein R is $C_{12}$-$C_{20}$ alkyl and M is an ion, preferably lauryl and myristyl sulfoacetates as sodium salts.

Many suitable anionic surfactants are commercially available from Stepan Company and are sold under the Alpha-Step®, Bio-Soft®, Bio-Terge®, Cedepal®, Nacconol®, Ninate®, Polystep®, Steol®, Stepanate®, Stepanol®, Stepantan®, and Steposol® trademarks. For further examples of suitable anionic surfactants, see U.S. Pat. No. 6,528,070, the teachings of which are incorporated herein by reference.

B. The Metathesis-Derived Cationic Surfactant

The second component of the inventive blend is a cationic surfactant comprising a quaternized derivative. The quaternized derivative is a quaternized fatty amine, quaternized fatty amidoamine, imidazoline quat, or esteramine quat. The quaternized derivative is made from a metathesis-derived $C_{10}$-$C_{17}$ monounsaturated acid or its ester derivative.

The skilled person will appreciate that "ester derivative" here encompasses other acyl equivalents, such as acid chlorides, acid anhydrides, or the like, in addition to the more common lower alkyl esters.

In one aspect, the ester derivative is a lower alkyl ester, especially a methyl ester. The lower alkyl esters are preferably generated by transesterifying a metathesis-derived triglyceride. For example, cross-metathesis of a natural oil with an olefin, followed by removal of unsaturated hydrocarbon metathesis products by stripping, and then transesterification of the modified oil component with a lower alkanol under basic conditions provides a mixture of unsaturated lower alkyl esters. The unsaturated lower alkyl ester mixture can be used "as is" to make quaternized derivatives or it can be purified to isolate particular alkyl esters prior to making the quaternized derivatives.

The $C_{10}$-$C_{17}$ monounsaturated acid or its ester derivative used as a reactant is derived from metathesis of a natural oil. Traditionally, these materials, particularly the short-chain acids and derivatives (e.g., 9-decylenic acid or 9-dodecylenic acid) have been difficult to obtain except in lab-scale quantities at considerable expense. However, because of the recent improvements in metathesis catalysts, these acids and their ester derivatives are now available in bulk at reasonable cost. Thus, the $C_{10}$-$C_{17}$ monounsaturated acids and esters are conveniently generated by cross-metathesis of natural oils with olefins, preferably α-olefins, and particularly ethylene, propylene, 1-butene, 1-hexene, 1-octene, and the like.

Preferably, at least a portion of the $C_{10}$-$C_{17}$ monounsaturated acid has "$\Delta^9$" unsaturation, i.e., the carbon-carbon double bond in the $C_{10}$-$C_{17}$ acid is at the 9-position with respect to the acid carbonyl. In other words, there are preferably seven carbons between the acid carbonyl group and the olefin group at C9 and C10. For the $C_{11}$ to $C_{17}$ acids, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty acids that have $\Delta^9$ unsaturation, e.g., oleic acid, usually have ~100% cis- isomers.

Although a high proportion of trans- geometry (particularly trans-$\Delta^9$ geometry) may be desirable in the metathesis-derived quaternized derivatives, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal. A: General* 346 (2009) 158, especially FIG. 3. Thus, the skilled person might modify the reaction conditions to control the degree of isomerization or alter the proportion of cis- and trans- isomers generated. For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated acid or ester) imparts different physical properties to quaternized derivatives made from them, including, for example, modified physical form, melting range, compactability, and other important properties. These differences should allow formulators that the quaternized derivatives greater latitude or expanded choice as they use the metathesis-derived cationic surfactants in cleaners, fabric treatment, personal care, agricultural uses, and other end uses.

Suitable metathesis-derived $C_{10}$-$C_{17}$ monounsaturated acids include, for example, 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like, and their ester derivatives.

Usually, cross-metathesis or self-metathesis of the natural oil is followed by separation of an olefin stream from a modified oil stream, typically by distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{18}$ alkyl esters, which are essentially spectators in the metathesis reaction. The rest of the product mixture depends on whether cross- or self-metathesis is used. When the natural oil is self-metathesized and then transesterified, the alkyl ester mixture will include a $C_{18}$ unsaturated diester. When the natural oil is cross-metathesized with an α-olefin and the product mixture is transesterified, the resulting alkyl ester mixture includes a $C_{10}$ unsaturated alkyl ester and one or more $C_{11}$ to $C_{17}$ unsaturated alkyl ester coproducts in addition to the glycerin by-product. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. The $C_{10}$ unsaturated alkyl ester is readily separated from the $C_{11}$ to $C_{17}$ unsaturated alkyl ester and each is easily purified by fractional distillation. These alkyl esters are excellent starting materials for making the quaternized derivatives.

Natural oils suitable for use as a feedstock to generate the $C_{10}$-$C_{17}$ monounsaturated acid or its ester derivative from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, tallow, lard, poultry fat, fish oil, and the like. Soybean oil, palm oil, rapeseed oil, and mixtures thereof are preferred natural oils.

Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty groups derived from oleic acid. Thus, particularly preferred natural oils include soybean oil, palm oil, algal oil, and rapeseed oil.

A modified natural oil, such as a partially hydrogenated vegetable oil, can be used instead of or in combination with the natural oil. When a natural oil is partially hydrogenated, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to quaternized derivatives.

An alternative to using a natural oil as a feedstock to generate the $C_{10}$-$C_{17}$ monounsaturated acid or its ester derivative from self-metathesis or cross-metathesis with olefins is a monounsaturated fatty acid obtained by the hydrolysis of a vegetable oil or animal fat, or an ester or salt of such an acid obtained by esterification of a fatty acid or carboxylate salt, or by transesterification of a natural oil with an alcohol. Also useful as starting compositions are polyunsaturated fatty esters, acids, and carboxylate salts. The salts can include an alkali metal (e.g., Li, Na, or K); an alkaline earth metal (e.g., Mg or Ca); a Group 13-15 metal (e.g., B, Al, Sn, Pb, or Sb), or a transition, lanthanide, or actinide metal. Additional suitable starting compositions are described at pp. 7-17 of PCT application WO 2008/048522, the contents of which are incorporated by reference herein.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

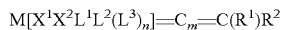

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first-and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

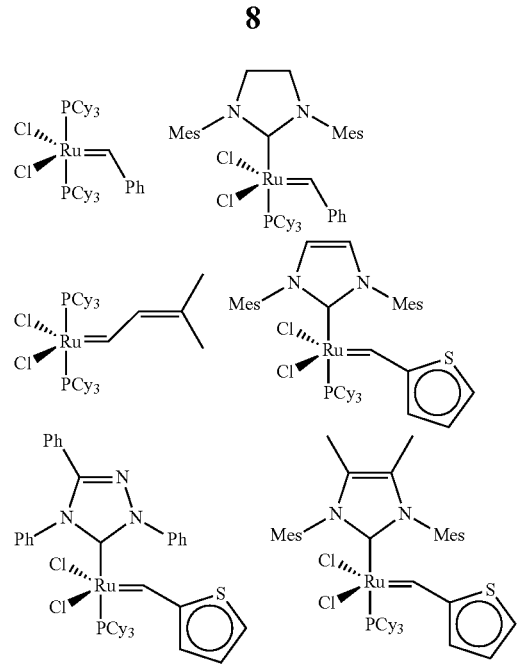

Heterogeneous catalysts suitable for use in the self- or cross-metathesis reaction include certain rhenium and molybdenum compounds as described, e.g., by J.C. Mol in Green Chem. 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein.

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. (The "C18-" series of products in the examples below, for instance, are nominally 100% trans-isomers whereas the "Mix-" series are nominally 80:20 trans-/cis-isomer mixtures.) Structures shown often refer to a principal product that may be accompanied by a lesser proportion of other components or positional isomers. For instance, sulfonation or sulfitation processes often give mixtures of sultones, alkanesulfonates, and alkenesulfonates, in addition to isomerized products. Thus, the structures provided represent likely or predominant products. Charges may or may not be shown but are understood, as in the case of amine oxide structures. Counterions, as in quaternized compositions, are not usually included, but they are understood by the skilled person from the context.

As noted above, the metathesis-based cationic surfactants comprise quaternized derivatives. The quaternized derivatives include quaternized fatty amines, quaternized fatty amidoamines, imidazoline quats, and esteramine quats.

1. Quaternized Fatty Amines and Fatty Amidoamines

Fatty amines used to make the quaternized fatty amines can be made by reacting a metathesis-derived $C_{10}$-$C_{17}$ monounsaturated acid or its ester derivative with a secondary amine, followed by reduction of the resulting fatty amide. They can also be made reducing a metathesis-derived acid or ester derivative to a fatty alcohol, followed by amination of the fatty alcohol. Thus, intermediates to the fatty amines are metathesis-derived fatty alcohols or fatty amides.

Suitable secondary amines have a hydrogen and two hydrocarbyl groups attached to nitrogen. The hydrocarbyl groups are preferably linear, branched, or cyclic $C_1$-$C_{20}$ alkyl, $C_6$-$C_{20}$ aryl, or $C_7$-$C_{20}$ arylalkyl. More preferably, both of the hydrocarbyl groups are $C_1$-$C_6$ alkyl groups. Suitable secondary amines include, for example, N,N-dimethylamine, N,N-diethylamine, N,N,-dipropylamine, diisopropylamine, N,N-dibutylamine, N-methyl-N-cyclohexylamine, N-methyl-N-phenylamine, N-methyl-N-benzylamine, or the like, and mixtures thereof. N,N-Dimethylamine is cost-effective and is particularly preferred.

Suitable secondary amines include etheramines. Thus, amines that are reaction products of ammonia or primary amines and an alkylene oxide, for example 0.1 to 20 molar equivalents of ethylene oxide, propylene oxide, or the like, can be used. The amine can be, for instance, a monoalkylated derivative of a Jeffamine® M series polyether amine (product of Huntsman). In some instances of using an etheramine, it may be necessary to mask any hydroxyl functionality as an appropriate derivative, either before or after formation of the amide, so as to enable the subsequent reduction of this amide.

The reactants are typically reacted, with or without a catalyst under conditions effective to convert the starting acid, ester, or other derivative to an amide. The reaction temperature is typically within the range of 40° C. to 300° C., preferably from 50° C. to 250° C., and more preferably from 50° C. to 200° C.

Reduction of the fatty amide to give a terminal amine is accomplished using well-known methods, including reactions with a hydride reducing agent (boranes, aluminum hydrides, borohydrides, or the like), or catalytic hydrogenation. Suitable reducing reagents include, for example, borane, borane dimethylsulfide, sodium borohydride/iodine, lithium cyanoborohydride, aluminum hydride, lithium aluminum hydride, diisobutylaluminum hydride, and the like. For additional examples, see R. Larock, *Comprehensive Organic Transformations: A Guide to Functional Group Preparations* (1989), pp. 432-434, and M. Smith and J. March, *March's Advanced Organic Chemistry*, 5th ed. (2001), pp. 1549-1550.

In an alternative synthetic approach, the fatty amine is made by first reducing the metathesis-derived acid or ester derivative to give a fatty alcohol, followed by amination of the fatty alcohol. The metathesis-derived acid or ester derivative is reduced to a fatty alcohol using a metal hydride reagent (sodium borohydride, lithium aluminum hydride, or the like), catalytic hydrogenation, or other well-known techniques for generating the fatty alcohol (see, e.g., U.S. Pat. Nos. 2,865,968; 3,193,586; 5,124,491; 6,683,224; and 7,208,643, the teachings of which are incorporated herein by reference). Amination is then preferably performed in a single step by reacting the fatty alcohol with ammonia or a primary or secondary amine in the presence of an amination catalyst. Suitable amination catalysts are well known. Catalysts comprising copper, nickel, and/or alkaline earth metal compounds are common. For suitable catalysts and processes for amination, see U.S. Pat. Nos. 5,696,294; 4,994,622; 4,594,455; 4,409,399; and 3,497,555, the teachings of which are incorporated herein by reference.

In a preferred aspect, the fatty amine is a fatty amidoamine made by reacting a metathesis-derived $C_{10}$-$C_{17}$ monounsaturated acid or its ester derivative with an aminoalkyl-substituted tertiary amine. This provides a product having tertiary amine functionality without the need to reduce a fatty amide to a fatty amine with a strong reducing agent. Suitable aminoalkyl-substituted tertiary amines have a primary amino group at one terminus, an alkylene group, and a tertiary amine group at the other end of the molecule. The alkylene group is preferably a $C_2$-$C_6$ linear or branched diradical such as ethylene, propylene, butylene, or the like. Thus, suitable aminoalkyl-substituted tertiary amines include, for example, N,N-dimethyl-1,2-ethanediamine, N,N-dimethyl-1, 3-propanediamine (DMAPA), N,N-diethyl-1,3-propanediamine, N,N-dimethyl-1, 4-butanediamine, and the like. DMAPA is particularly preferred. The primary amine group exhibits good reactivity with the acid or ester derivative, while the terminal tertiary amine is preserved in the product and provides a site for quaternization.

The relative amounts of secondary amine or aminoalkyl-substituted tertiary amine reacted with the ester or acid reactants depends on the desired stoichiometry and is left to the skilled person's discretion. In general, enough of the secondary amine (or aminoalkyl-substituted tertiary amine) is used to react with most or all of the available acid or ester groups, i.e., preferably greater than 90%, and more preferably greater than 95%, of the available acid or ester groups.

The tertiary amine group of the fatty amine or fatty amidoamine is quaternized to give a quaternary ammonium composition ("quaternized fatty amine" or "quaternized fatty amidoamine"). Suitable quaternizing methods and reagents are well known in the art. Common reagents include, for example, alkyl halides (methyl chloride, methyl bromide), dialkyl sulfates, carbonates, or phosphates (dimethyl sulfate, diethyl sulfate, dimethyl carbonate), benzyl chloride, acetyl chloride, ethylene oxide, and the like.

Some quaternized fatty amines have the formula:

wherein:

$R^1$ is —$C_{10}H_{18}$—$R^5$ or —$C_{18}H_{34}$—N+($R^2$)($R^3$)$R^4$ $X^-$; each of $R^2$ and $R^3$ is independently substituted or unsubstituted alkyl, aryl, alkenyl, oxyalkylene, or polyoxyalkylene; $R^4$ is $C_1$-$C_6$ alkyl; $X^-$ is a halide, bicarbonate, bisulfate, or alkyl sulfate; and $R^5$ is hydrogen or $C_1$-$C_7$ alkyl. Preferably, $R^1$ is —$(CH_2)_8$—CH=CH$R^5$ or —$(CH_2)_8$—CH=CH—$(CH_2)_8$—N+($R^2$)($R^3$)$R^4$ $X^-$.

Some quaternized fatty amidoamines have the formula:

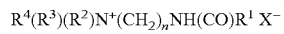

wherein: $R^1$ is —$C_9H_{16}$—$R^5$ or —$C_{16}H_{30}$—(CO)NH$(CH_2)_n$N+($R^2$)($R^3$)$R^4$ $X^-$; each of $R^2$ and $R^3$ is independently substituted or unsubstituted alkyl, aryl, alkenyl, oxyalkylene, or polyoxyalkylene; $R^4$ is $C_1$-$C_6$ alkyl; $X^-$ is a halide, bicarbonate, bisulfate, or alkyl sulfate; $R^5$ is hydrogen or $C_1$-$C_7$ alkyl; and n=2 to 8. Preferably, $R^1$ is —$(CH_2)_7$—CH=CH—$R^5$ or —$(CH_2)_7$—CH=CH—$(CH_2)_7$—(CO)NH$(CH_2)_n$N+($R^2$)($R^3$)$R^4$ $X^-$.

Specific examples of $C_{10}$, $C_{12}$, $C_{14}$, and $C_{16}$-based quaternized fatty amines and fatty amidoamines appear below:

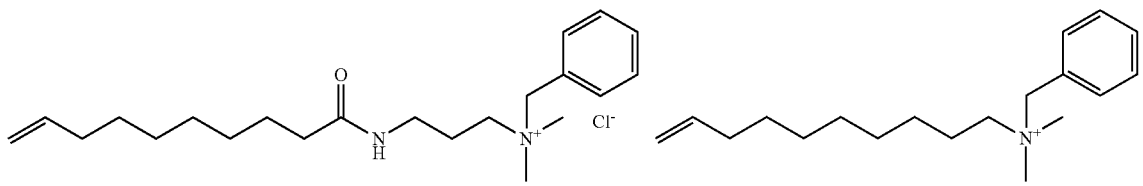

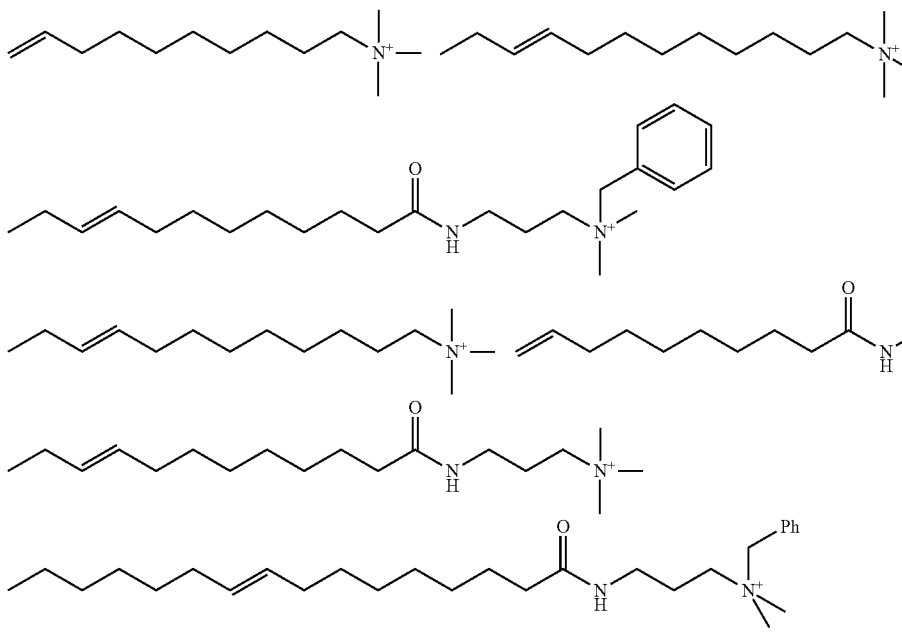

2. Imidazoline Quats

Suitable imidazolines (precursors to imidazoline quats) are made by reacting a metathesis-derived $C_{10}$-$C_{17}$ monounsaturated acid or its ester derivative with diethylene triamine (DETA), (2-aminoethyl)ethanolamine (AEEA), or an alkoxylated derivative thereof. DETA and AEEA can react with two equivalents of a $C_{10}$-$C_{17}$ monounsaturated acid or its ester derivative to give an imidazoline amide or ester, respectively, which have a tertiary nitrogen available for quaternization.

The starting ester is commonly heated with a tertiary amine catalyst (e.g., DABCO, 1,4-diazabicyclo[2.2.2]octane), and DETA or AEEA at 80° C. to 250° C. Additional DETA or AEEA is added to the reactor as needed. When the initial reaction is complete (as is usually indicated by no further distillate of an alcohol), an acid catalyst such as p-toluenesulfonic acid is added, and the mixture is heated at elevated temperature (e.g., 150° C. to 300° C., preferably from 180° C. to 250° C.) to effect the desired ring closure. Preferably, two moles of $C_{10}$ to $C_{17}$ acid or ester derivative per mole of DETA or AEEA are used to enable production of an imidazoline.

Quaternization of the imidazolines is accomplished by warming them with a quaternizing agent such as an alkyl halide or dialkyl sulfate. Specific examples include dimethylsulfate, methyl chloride, epichlorohydrin, benzyl chloride, alkali metal chloroacetates, and the like. Dimethyl sulfate is particularly preferred. The reaction is generally performed at a temperature within the range of 30° C. to 150° C., preferably from 65° C. to 100° C., or more preferably from 80° C. to 90° C. The amount of quaternizing agent used is typically 0.8 to 1.2 mole equivalents based on the tertiary nitrogen content. The reaction is deemed complete when the free amine value is in the desired range as determined by perchloric acid titration or other suitable analytical method. Suitable methods for quaternizing imidazolines are disclosed in U.S. Pat. Nos. 5,750,492; 5,783,534; 5,939,059; and 6,004,913, the teachings of which are incorporated herein by reference.

Examples of suitable $C_{10}$, $C_{12}$, $C_{14}$, and $C_{16}$-based quaternized imidazolines:

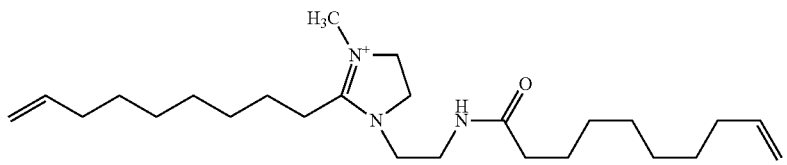

-continued

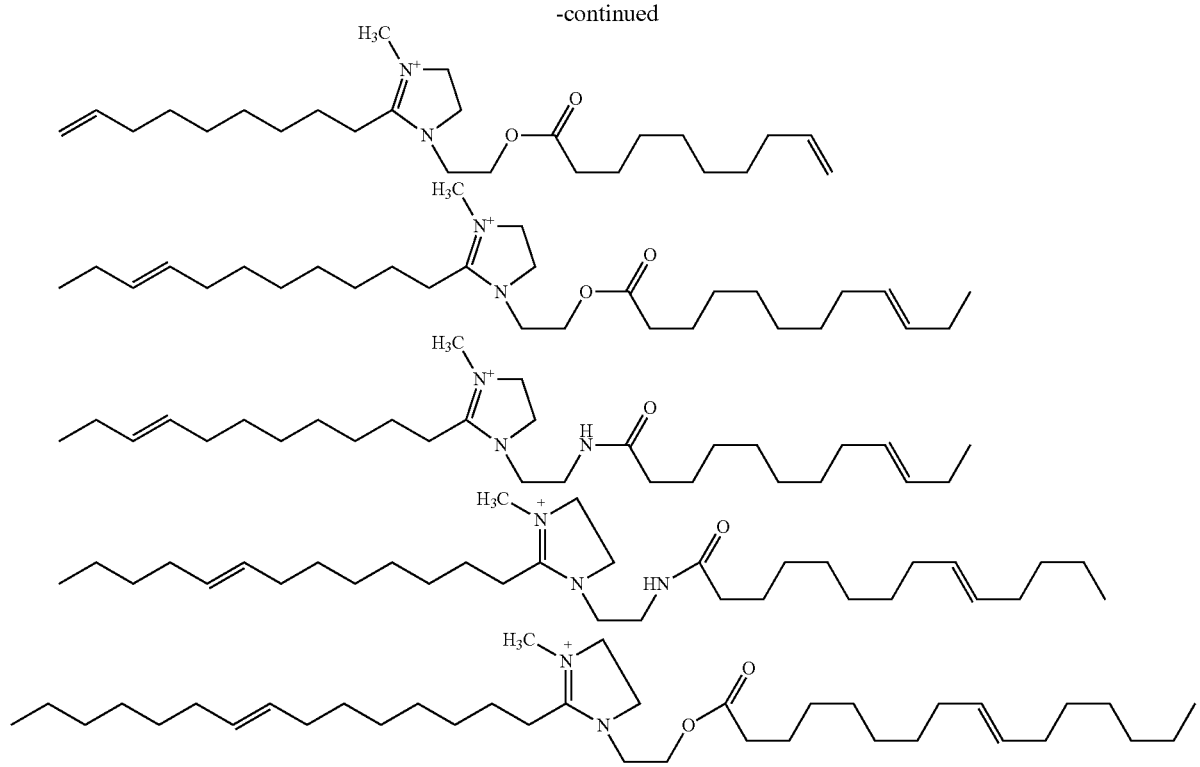

3. Esteramine Quats

Suitable esteramines (precursors to the esteramine quats) are made by reacting a metathesis-derived $C_{10}$-$C_{17}$ mono-unsaturated acid or its ester derivative with a tertiary alkanolamine.

Suitable tertiary alkanolamines have a tertiary amine group and from one to three primary or secondary hydroxyl groups. In preferred alkanolamines, the tertiary nitrogen is attached to zero, one, or two $C_1$-$C_{10}$ alkyl groups, preferably $C_1$-$C_4$ alkyl groups, and from one to three hydroxyalkyl groups having from 2 to 4 carbons each, where the total number of alkyl and hydroxyalkyl groups is three. Suitable alkanolamines are well known and commercially available from BASF, Dow Chemical and other suppliers. They include, for example, triethanolamine, N-methyldiethanolamine, N,N-dimethylethanolamine, N,N-dimethylpropanolamine, N,N-dimethylisopropanolamine, N-methyldiisopropanolamine, N,N-diethylethanolamine, triisopropanolamine, and the like, and mixtures thereof. Particularly preferred alkanolamines are triethanolamine, N-methyldiethanolamine, and N,N-dimethylethanolamine, which are economical and readily available.

Suitable alkanolamines include alkoxylated derivatives of the compounds described above. Thus, for example, the alkanolamine used to make the esteramine can be a reaction product of an alkanolamine with 0.1 to 20 moles of ethylene oxide or propylene oxide per mole of —OH groups in the alkanolamine.

The esteramines are made using a well-known process that provides a unique product mixture because of the unconventional starting mixture of acid or ester derivatives. The reactants are typically heated, with or without a catalyst under conditions effective to esterify or transesterify the starting acid or ester with the tertiary alkanolamine. The reaction temperature is typically within the range of 80° C. to 300° C., preferably from 150° C. to 200° C., and more preferably from 165° C. to 180° C.

The relative amounts of alkanolamine and ester or acid reactants used depend on the desired stoichiometry and is left to the skilled person's discretion. Preferably, however, the equivalent ratio of acyl groups (in the metathesis-derived acid or ester derivative) to hydroxyl groups (in the tertiary alkanolamine) is within the range of 0.1 to 3, preferably from 0.3 to 1. The ratio is frequently about 1, but lower acyl:hydroxyl equivalent ratios are also common.

Some esteramines have the formula:

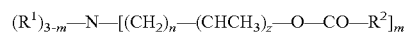

wherein:

$R^1$ is $C_1$-$C_6$ alkyl; $R^2$ is —$C_9H_{16}$—$R^3$ or —$C_{16}H_{30}$—$CO_2R^4$; $R^3$ is hydrogen or $C_1$-$C_7$ alkyl; $R^4$ is substituted or unsubstituted alkyl, aryl, alkenyl, oxyalkylene, polyoxyalkylene, glyceryl ester, or a mono- or divalent cation; m=1-3; n=1-4; z=0 or 1; and when z=0, n=2-4.

Preferably, $R^2$ is —$(CH_2)_7$—CH=$CHR^3$ or —$(CH_2)_7$—CH=CH—$(CH_2)_7$—$CO_2R^4$.

Esteramines are reacted with a quaternizing agent to give the esteramine quats according to well-known methods. Typically, the esteramine is warmed with a quaternizing agent such as an alkyl halide or dialkyl sulfate. Specific examples include dimethylsulfate, methyl chloride, epichlorohydrin, benzyl chloride, alkali metal chloroacetates, and the like. Dimethyl sulfate and benzyl chloride are particularly preferred. The reaction is generally performed at a temperature within the range of 30° C. to 150° C., preferably from 65° C. to 100° C., or more preferably from 80° C. to 90° C. The amount of quaternizing agent used is typically 0.8 to 1.0 mole equivalents based on the tertiary nitrogen content. The reaction is deemed complete when the free amine value is in the desired range as determined by perchloric acid titration. Suitable methods for quaternizing the esteramines are disclosed in U.S. Pat. Nos. 5,750,492; 5,783,534; 5,939,059; and 6,004,913, the teachings of which are incorporated herein by reference.

Examples of suitable $C_{10}$, $C_{12}$, $C_{14}$, and $C_{16}$-based quaternized esteramines ("ester quats"):

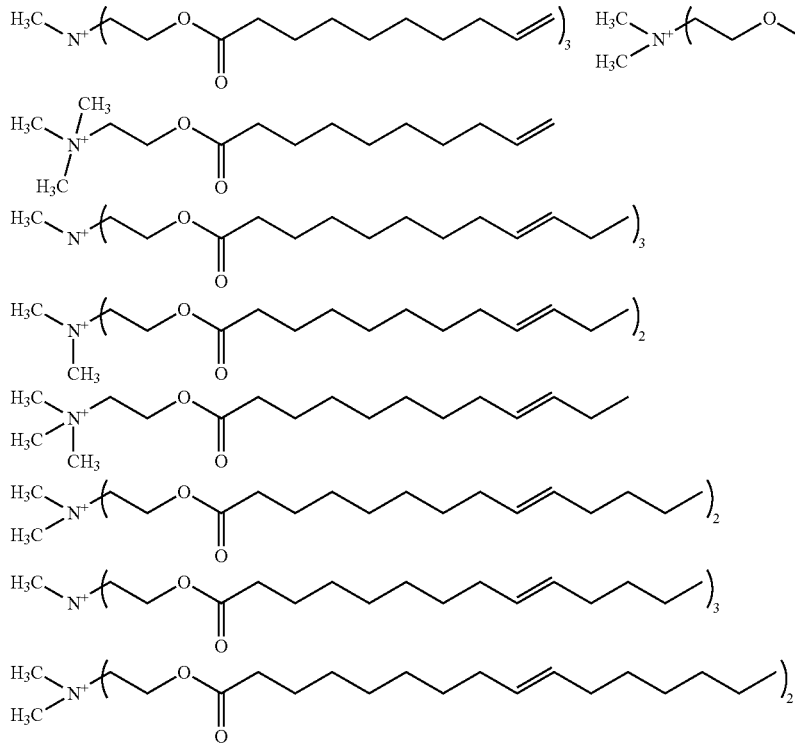

wherein the short chain alkyl groups can be the same or different but preferably are independently methyl or ethyl. Specific examples include cetyl trimethyl ammonium chloride and lauryl trimethyl ammonium chloride. Preferred cationic surfactants include octyltrimethyl ammonium chloride, decyltrimethyl ammonium chloride, dodecyltrimethyl ammonium bromide, dodecyltrimethyl ammonium chloride, and the like. Cetrimonium chloride (hexadecyltrimethylammonium chloride) supplied as Ammonyx® Cetac 30, product of Stepan Company) is a preferred example.

Salts of primary, secondary and tertiary fatty amines are also suitable cationic surfactants. The alkyl groups of such amine salts preferably have from about 12 to about 22 carbon atoms, and may be substituted or unsubstituted. Secondary and tertiary amine salts are preferred, and tertiary amine salts are particularly preferred. Suitable amine salts include the halogen, acetate, phosphate, nitrate, citrate, lactate and alkyl sulfate salts. Salts of, for example, stearamidopropyl dimethyl amine, diethylaminoethyl stearamide, dimethyl stearamine, dimethyl soyamine, soyamine, myristyl amine, tridecylamine, ethyl stearylamine, N-tallowpropane diamine, ethoxylated stearylamine, stearylamine hydrogen chloride, soyamine chloride, stearylamine formate, N-tallowpropane diamine dichloride stearamidopropyl dimethylamine citrate, and the like are useful herein.

Suitable cationic surfactants include imidazolines, imidazoliniums, and pyridiniums, and the like, such as, for example, 2-heptadecyl-4,5-dihydro-1H-imidazol-1-ethanol, 4,5-dihydro-1-(2-hydroxyethyl)-2-isoheptadecyl-1phenyl-methylimidazolium chloride, and 1-[2-oxo-2-[[2-[(1-oxoctadecyl)oxy]ethyl]-amino]ethyl]pyridinium chloride. For more examples, see U.S. Pat. No. 6,528,070, the teachings of which are incorporated herein by reference. Other suitable cationic surfactants include quaternized esteramines or II. Synergistic Surfactant Blend: Metathesis-Based Anionic Surfactant Another synergistic surfactant blend of the invention comprises a metathesis-based anionic surfactant. This blend comprises a cationic surfactant and an anionic surfactant comprising a sulfonated derivative. The sulfonated derivative is selected from fatty ester sulfonates, fatty acid sulfonates, sulfoestolides, fatty amide sulfonates, sulfonated fatty ester alkoxylates, imidazoline quat sulfonates, sulfonated amidoamine oxides, and sulfonated amidoamine betaines. The sulfonated derivative is made from a metathesis-derived $C_{10}$-$C_{17}$ monounsaturated acid, octadecene-1,18-dioic acid, or their ester derivatives.

A. The Cationic Surfactant

Suitable cationic surfactants include fatty amine salts (including diamine or polyamine salts), quaternary ammonium salts, salts of fatty amine ethoxylates, quaternized fatty amine ethoxylates, and the like, and mixtures thereof. Useful cationic surfactants are disclosed in *McCutcheon's Detergents & Emulsifiers* (M.C. Publishing, N. American Ed., 1993); Schwartz et al., *Surface Active Agents, Their Chemistry and Technology* (New York: Interscience, 1949) and in U.S. Pat. Nos. 3,155,591; 3,929,678; 3,959,461; 4,275,055; and 4,387,090. Suitable anions include halogen, sulfate, methosulfate, ethosulfate, tosylate, acetate, phosphate, nitrate, sulfonate, carboxylate, and the like.

Suitable quaternary ammonium salts include mono-long chain alkyl-tri-short chain alkyl ammonium halides, wherein the long chain alkyl group has from about 8 to about 22 carbon atoms and is derived from long-chain fatty acids, and "ester quats," and as disclosed in U.S. Pat. No. 5,939,059, the teachings of which are incorporated herein by reference. The cationic surfactant may be a DMAPA or other amido-amine-based quaternary ammonium material, including diamidoamine quats. It may also be a di- or poly-quaternary compound (e.g., a diester quat or a diamidoamine quat). Anti-microbial compounds, such as alkyldimethylbenzyl ammonium halides or their mixtures with other quaternary compounds, are also suitable cationic surfactants. An example is a mixture of an alkyl dimethylbenzyl ammonium chloride and an alkyl dimethyl ethylbenzylammonium chloride, available commercially from Stepan Company as BTC® 2125M.

Many suitable cationic surfactants are commercially available from Stepan Company and are sold under the Ammonyx®, Accosoft®, Amphosol®, BTC®, Stepanquat®, and Stepantex® trademarks. For further examples of suitable cationic surfactants, see U.S. Pat. No. 6,528,070, the teachings of which are incorporated herein by reference.

B. The Metathesis-Derived Anionic Surfactant

The metathesis-derived anionic surfactant comprises a sulfonated derivative selected from the group consisting of fatty ester sulfonates, fatty acid sulfonates, sulfoestolides, fatty amide sulfonates, sulfonated fatty ester alkoxylates, imidazoline quat sulfonates, sulfonated amidoamine oxides, and sulfonated amidoamine betaines. The sulfonated derivative is made from a metathesis-derived $C_{10}$-$C_{17}$ monounsaturated acid, octadecene-1,18-dioic acid, or their ester derivatives.

The metathesis-derived $C_{10}$-$C_{17}$ monounsaturated acid and its derivatives described in Section I.B. (above) are also useful for making metathesis-derived anionic surfactants. Thus, for a description of suitable feedstocks for making the metathesis-based anionic surfactants, as well as suitable raw materials and metathesis catalysts, see Section I.B. Some of the metathesis-derived sulfonated derivatives can be made from octadecene-1,18-dioic acid or its ester derivatives. The diacid is available from natural oil self-metathesis according to well-known procedures (see preparation of diesters C18-0 and Mix-0 below).

1. Fatty Acid Sulfonates and Fatty Ester Sulfonates

These sulfonates are made by reacting a metathesis-derived $C_{10}$-$C_{17}$ monounsaturated acid, octadecene-1,18-dioic acid, or their ester derivatives with a sulfonating or sulfitating agent.

Sulfonation is performed using well-known methods, including reacting the olefin with sulfur trioxide. Sulfonation may optionally be conducted using an inert solvent. Non-limiting examples of suitable solvents include liquid $SO_2$, hydrocarbons, and halogenated hydrocarbons. In one commercial approach, a falling film reactor is used to continuously sulfonate the olefin using sulfur trioxide. Other sulfonating agents can be used with or without use of a solvent (e.g., chlorosulfonic acid, fuming sulfuric acid), but sulfur trioxide is generally the most economical. The sultones that are the immediate products of reacting olefins with $SO_3$, chlorosulfonic acid, and the like may be subsequently subjected to a hydrolysis reaction with aqueous caustic to afford mixtures of alkene sulfonates and hydroxyalkane sulfonates. Suitable methods for sulfonating olefins are described in U.S. Pat. Nos. 3,169,142; 4,148,821; and U.S. Pat. Appl. Publ. No. 2010/0282467, the teachings of which are incorporated herein by reference.

Sulfitation is accomplished by combining an olefin in water (and usually a cosolvent such as isopropanol) with at least a molar equivalent of a sulfitating agent using well-known methods. Suitable sulfitating agents include, for example, sodium sulfite, sodium bisulfite, sodium metabisulfite, or the like. Optionally, a catalyst or initiator is included, such as peroxides, iron, or other free-radical initiators. Typically, the reaction mixture is conducted at 15-100° C. until the reaction is reasonably complete. Suitable methods for sulfitating olefins appear in U.S. Pat. Nos. 2,653,970; 4,087,457; 4,275,013, the teachings of which are incorporated herein by reference.

Sulfonation or sulfitation of the metathesis-derived $C_{10}$-$C_{17}$ monounsaturated acid, octadecene-1,18-dioic acid, or their ester derivatives provides reaction products that include one or more of alkanesulfonates, alkenesulfonates, sultones, hydroxy-substituted alkanesulfonates. Mixtures of these reaction products are typical (see, e.g., sulfonates C10-1 and C12-1, in the examples below).

Some preferred alkanesulfonates have the structure:

$$XO_3S\text{---}[C_nH_{2n}CO_2R]$$

wherein X is H, an alkali metal, ammonium, or alkylammonium cation; R is X or $C_1$-$C_{10}$ alkyl or aryl; n=9-16; and the S atom is bonded to any carbon on the $C_nH_{2n}$ chain. Preferably, the S atom is bonded at the C9 or C10 position relative to the carbonyl carbon. Preferably, the $C_nH_{2n}$ chain is linear. When n=9, the S atom is bonded to C10.

Additional preferred alkanesulfonates have the structure:

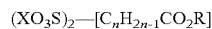

$$(XO_3S)_2\text{---}[C_nH_{2n-1}CO_2R]$$

wherein X is H, an alkali metal, ammonium, or alkylammonium cation; R is X or $C_1$-$C_{10}$ alkyl or aryl; n=9-16; and the S atoms are bonded to any pair of adjacent carbons on the $C_nH_{2n-1}$ chain. Preferably, the S atoms are bonded at the C9 and C10 positions relative to the carbonyl carbon. Preferably, the $C_nH_{2n-1}$ chain is linear. When n=9, an S atom is bonded to C10.

Some preferred alkenesulfonates have the structure:

$$XO_3S\text{---}[C_nH_{2n-2}CO_2R]$$

wherein X is H, an alkali metal, ammonium, or alkylammonium cation; R is X or $C_1$-$C_{10}$ alkyl or aryl; n=9-16; and the S atom is bonded to any carbon on the $C_nH_{2n-2}$ chain. Preferably, the S atom is bonded at the C9 or C10 position relative to the carbonyl carbon. In more preferred alkenesulfonates, the S atom is bonded at the C9 or C10 position and the unsaturation is allylic with respect to sulfur. Preferably, the $C_nH_{2n-2}$ chain is linear. When n=9, the S atom is bonded to C10.

Some preferred hydroxyalkanesulfonates have the structure:

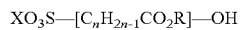

$$XO_3S\text{---}[C_nH_{2n-1}CO_2R]\text{---}OH$$

wherein X is H, an alkali metal, ammonium, or alkylammonium cation; R is X or $C_1$-$C_{10}$ alkyl or aryl; n=9-16; the S atom is bonded to any carbon on the $C_nH_{2n-1}$ chain, and the OH group is bonded to a carbon that is α, β, or γ relative to the carbon that is substituted with the —$SO_3X$ group. Preferably, the S atom is bonded at the C9 or C10 position relative to the carbonyl carbon. Preferably, the $C_nH_{2n-1}$ chain is linear. When n=9, the S atom is bonded to C10.

Preferred sultones are β-, γ-, or δ-sultones, which have four, five, or six-membered rings, respectively, that incorporate a —$SO_2$—O— group within the ring. As the skilled person appreciates, the sultones are typically intermediates that, through appropriate processing conditions such as treatment with aqueous alkali, may be converted to hydroxyalkanesulfonates and/or alkenesulfonates.

Some specific examples of $C_{10}$, $C_{12}$ and $C_{16}$-based sulfonate mixtures appear below:

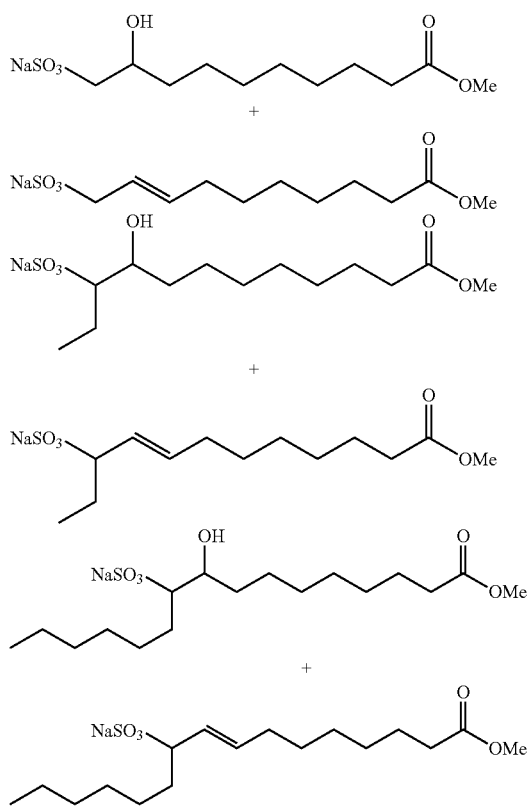

2. Sulfoestolides

Suitable sulfonated derivatives include sulfo-estolides made by reacting a metathesis-derived $C_{10}$-$C_{17}$ monounsaturated acid or octadecene-1,18-dioic acid with a sulfonating agent. Optionally, the sulfo-estolide is made by reacting the metathesis-derived $C_{10}$-$C_{17}$ monounsaturated acid, octadecene-1,18-dioic acid, or their ester derivatives with a sulfonating agent in the presence of an additional carboxylic acid. The additional carboxylic acid can be saturated or unsaturated and branched or unbranched. In some instances, the additional carboxylic acid is preferably a saturated $C_6$ to $C_{18}$ carboxylic acid. Suitable sulfo-estolides have the structural moiety:

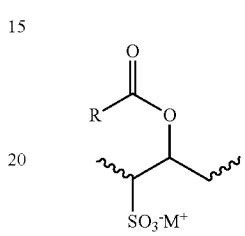

in which R is a linear or branched, saturated or unsaturated, substituted or unsubstituted alkyl radical and M is hydrogen or a mono or divalent cation (shown as monovalent above) such as sodium, potassium, calcium, trialkanolammonium, or the like.

Sulfonation converts some of the carbon-carbon double bonds in the metathesis-derived acid or ester reactant to sultones, particularly β-sultones. These are believed to undergo nucleophilic attack by a carboxylic oxygen to give a sulfo-estolide. The scheme below depicts a possible reaction pathway using a $C_{10}$ unsaturated fatty acid as the reactant:

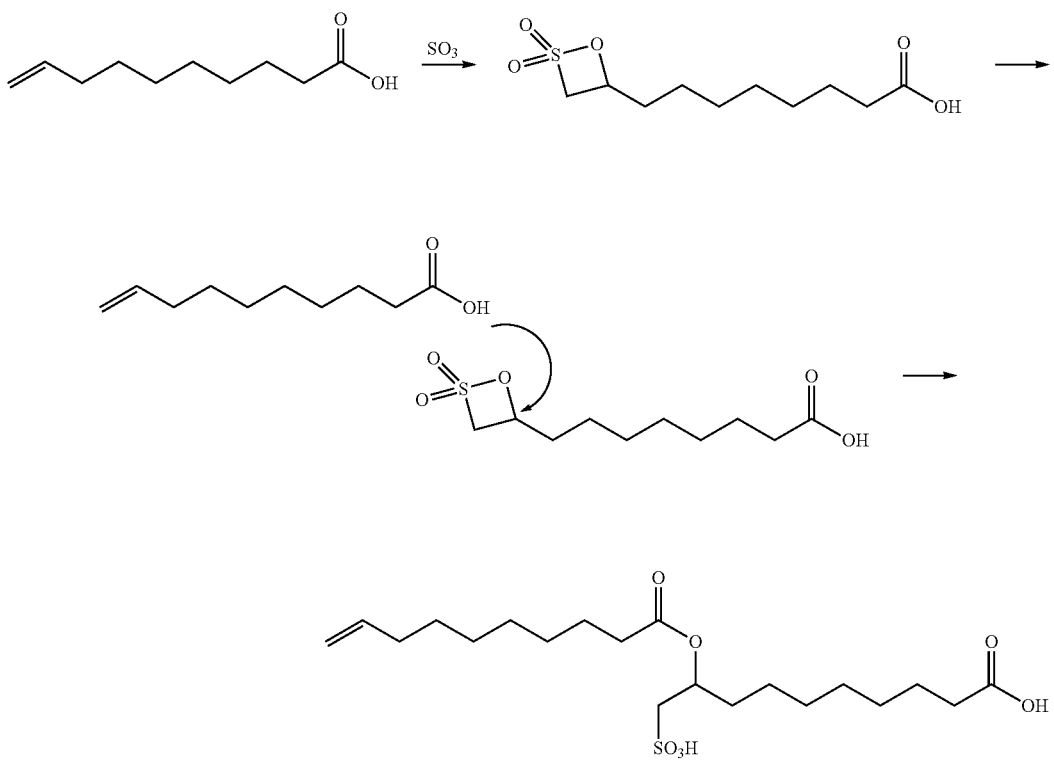

As the skilled person will appreciate, the product mixture will be more complex than shown above, for example, when the starting material is a mixture of different unsaturated acids and/or esters, or when the sulfonation is performed under conditions that promote isomerization of the carbon-carbon double bond.

The product mixture may comprise oligomers, for example dimers and trimers that are formed by the ring-opening of β-sultone with carboxlic acids of sulfo-estolides. The degree of oligomerization is optionally controlled by adjusting the proportion of saturated and unsaturated fatty acid components, as the saturated fatty acid serves as a chain terminator. For examples of reactions used to produce sulfo-estolides, see U.S. Pat. Nos. 7,879,790 and 7,666,828 and U.S. Pat. Appl. Publ. No. 2010/0016198, the teachings of which are incorporated herein by reference.

Some sulfo-estolides have the structure:

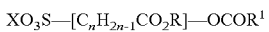

wherein X is H, an alkali metal, ammonium, or alkylammonium cation; R is X or $C_1$-$C_{10}$ alkyl or aryl; n=9-16; $R^1$ is a $C_8$ to $C_{18}$ saturated or monounsaturated group. The S atom and the —OCOR$^1$ group are bonded to vicinal carbons on the $C_nH_{2n-1}$ chain. When n=9, the S atom is preferably bonded at the C10 position relative to the carbonyl carbon. Some specific examples of sulfo-estolides:

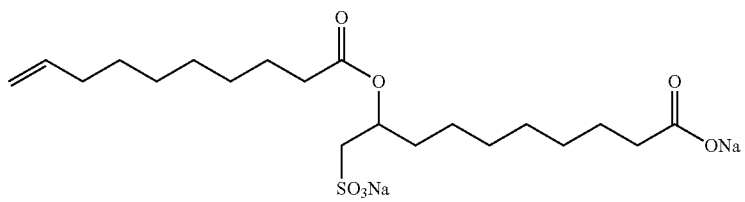

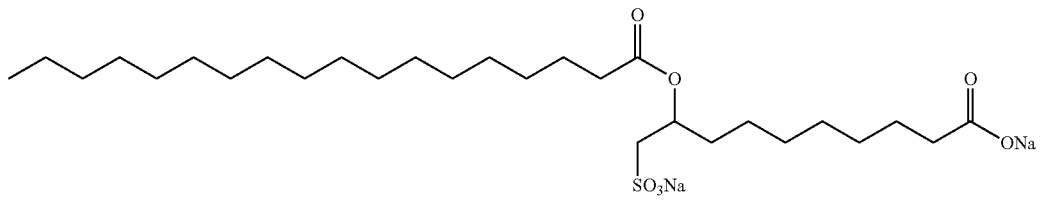

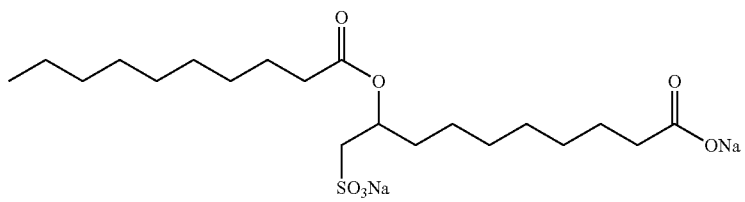

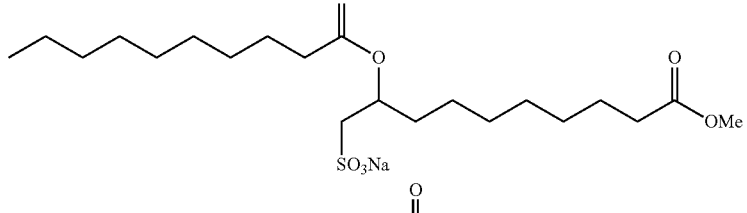

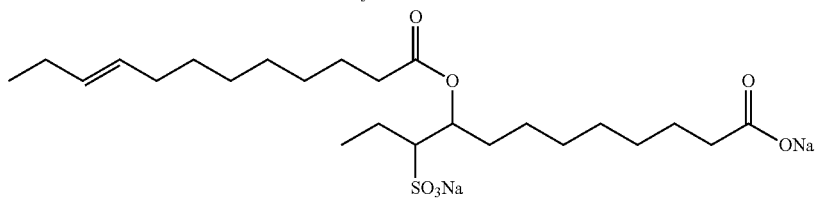

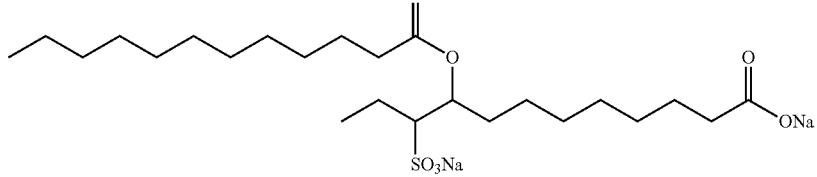

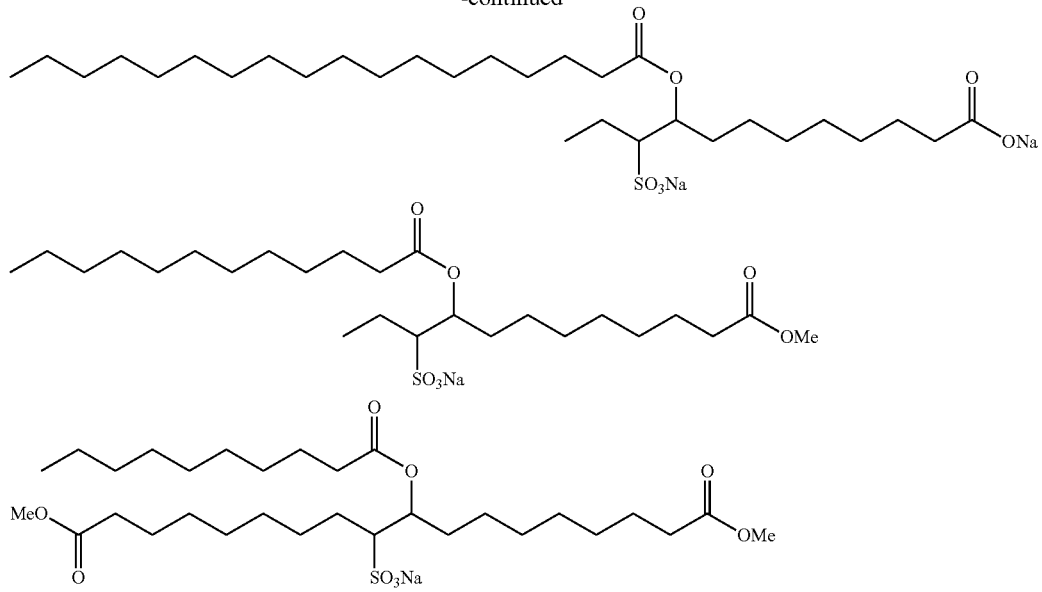

3. Fatty Amide Sulfonates

The fatty amides (precursors to the fatty amide sulfonates) are made by reacting a metathesis-derived $C_{10}$-$C_{17}$ mono-unsaturated acid, octadecene-1,18-dioic acid, or their ester derivatives with ammonia or a primary or secondary amine.

Suitable primary or secondary amines have one or two hydrogens attached to the amino group. The remaining groups are typically alkyl or substituted alkyl groups, preferably $C_1$-$C_{10}$ alkyl, more preferably $C_1$-$C_4$ alkyl. Thus, suitable primary or secondary amines include ethylamine, isopropylamine, N,N-dimethylamine, N,N-diethylamine, N,N-diisopropylamine, and the like. In one preferred class of primary and secondary amines, a N or O atom is bonded to a carbon that is beta or gamma to the N atom of the amine. In some preferred primary or secondary amines, the nitrogen is attached to one $C_1$-$C_{10}$ alkyl group, preferably a $C_1$-$C_4$ alkyl group, and one hydroxyalkyl group having from 2 to 4 carbons. In other preferred primary or secondary amines, the nitrogen is attached to a hydrogen and two hydroxyalkyl groups having from 2 to 4 carbons each. Alkanolamines, which have an oxygen atom beta to the amine nitrogen, are particularly preferred. Suitable alkanolamines are well known and commercially available from BASF, Dow Chemical and other suppliers. They include, for example, ethanolamine, propanolamine, isopropanolamine, diethanolamine, N-methylethanolamine, N-methylisopropanolamine, N-ethylethanolamine, and the like, and mixtures thereof. Particularly preferred alkanolamines are ethanolamine, diethanolamine, and N-methylethanolamine, which are economical and readily available.

Suitable primary and secondary amines include alkoxylated derivatives of the compounds described above. Thus, for example, the amine used to make the fatty amide can be an amine-terminated polyether comprising 0.1 to 20 moles of ethylene oxide or propylene oxide per mole of —OH group in the alkanolamine.

Some amides have the formula:

$R^1CO—NR^2R^3$ where $R^1$ is $R^4$—$C_9H_{16}$— or $R^5O_2C$—$C_{16}H_{30}$—; $R^4$ is hydrogen or $C_1$-$C_7$ alkyl; $R^5$ is substituted or unsubstituted alkyl, aryl, alkenyl, oxyalkylene, polyoxyalkylene, glyceryl ester, or a mono- or divalent cation; and each of $R^2$ and $R^3$ is independently H, $C_1$-$C_6$ alkyl, or —$CH_2CH_2OR^6$ where $R^6$ is H or $C_1$-$C_6$ alkyl. Preferably, $R^1$ is $R^4CH{=}CH—(CH_2)_7$— or $R^5O_2C—(CH_2)_7$—$CH{=}CH—(CH_2)_7$—.

Some specific examples of $C_{10}$, $C_{12}$, $C_{14}$, and $C_{16}$-based fatty amides appear below:

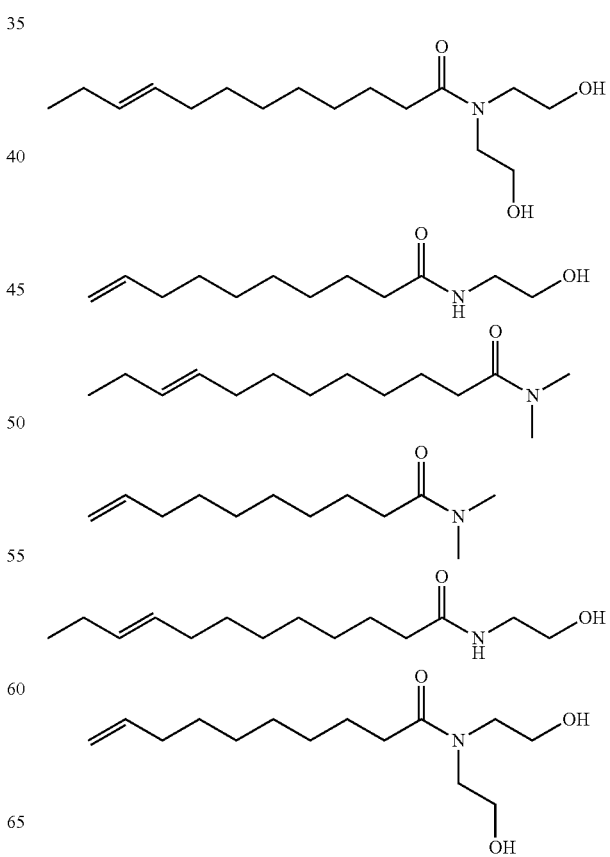

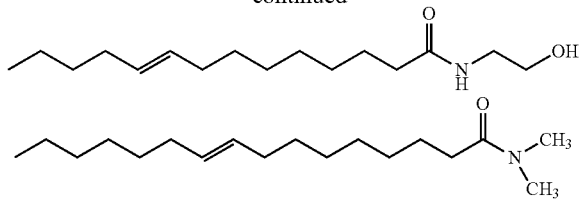

The corresponding fatty amide sulfonates are made by reacting the above-mentioned fatty amides with a sulfonating or sulfitating agent, generally as previously described in Section II.B.1, above.

Exemplary fatty amide sulfonates:

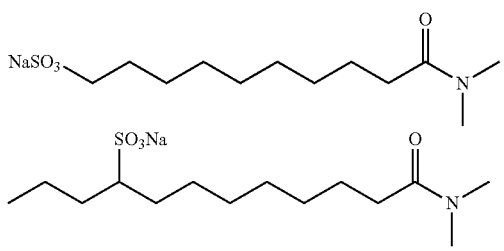

4. Sulfonated Fatty Ester Alkoxylates

Suitable alkoxylated fatty esters (precursors to the sulfonated fatty ester alkoxylates) comprise a reaction product of a metathesis-derived $C_{10}$-$C_{17}$ monounsaturated acid, octadecene-1,18-dioic acid, or their ester derivatives with one or more alkylene oxides in the presence of an insertion catalyst to give an alkoxylated fatty ester. Alternatively, the metathesis-derived starting material is reacted with a glycol ether or a glycol ether alkoxylate, optionally in the presence of an esterification or transesterification catalyst, to give the alkoxylated fatty ester. In yet another alternative, the metathesis-derived starting material is reacted with one or more alkylene oxides to give a fatty acid alkoxylate, followed by etherification of the fatty acid alkoxylate.

Preferably, the alkoxylated fatty ester composition comprises a product made by reacting the metathesis-derived feedstock with one or more alkylene oxides in the presence of an insertion catalyst.

Suitable alkylene oxides are $C_2$-$C_4$ alkylene oxides, particularly ethylene oxide, propylene oxide, and butylene oxides. Ethylene oxide and propylene oxide are preferred. Ethylene oxide is particularly preferred. Mixtures or combinations of different alkylene oxides can be used if desired to generate a random distribution or a block of alkylene oxide units.

The selection of alkylene oxide(s) and the proportion used relative to the amount of metathesis-derived acid or ester depends on the desired performance characteristics of the product and is within the skilled person's discretion. Preferably, n, which is the average number of oxyalkylene units in the alkoxylated fatty ester, is within the range of 1 to 100.

Preferably, ethylene oxide units are incorporated to enhance hydrophilicity of the composition when compared with the starting metathesis-derived acid or ester. When relatively low hydrophilicity is desired, n typically ranges from 1 to 5 EO units. For intermediate hydrophilicity, n typically ranges from 5 to 15 EO units, and for higher hydrophilicity, n typically ranges from 15 to 50 EO units.

Suitable insertion catalysts are well known. They include, for example, modified or composite metal oxides, such as magnesium oxide modified with aluminum, gallium, zirconium, lanthanum, or other transition metals, calcined hydrotalcites, calcined aluminum magnesium hydroxides, and the like. Composite oxide catalysts comprising magnesium and aluminum are preferred. Usually, the metathesis-derived fatty acid or ester is reacted in the presence of the alkylene oxide(s) and insertion catalyst and under predetermined temperature and pressure conditions, typically under nitrogen or other inert atmosphere, and the alkoxylated product is then isolated and purified by known methods. For particular examples of suitable insertion catalysts and process details for making alkoxylated fatty esters by alkylene oxide insertion, see U.S. Pat. Nos. 5,817,844, 6,184,400, and 6,504,061, the teachings of which are incorporated herein by reference. The reaction is considered complete when the product gives satisfactory analysis. For example, in the $^1$H NMR spectrum, the chemical shift of the methylene group located alpha to the carbonyl can be used to differentiate unreacted starting material from alkoxylated product.

Some inventive alkoxylated fatty esters have the formula:

$R^2$—CO—O-(AO)$_n$—$R^1$ wherein $R^1$ is $C_1$-$C_4$ alkyl; AO is $C_2$-$C_4$ oxyalkylene; $R^2$ is $R^3$—$C_9H_{16}$— or $R^1$(AO)$_n$O—CO—$C_{16}H_{30}$—; $R^3$ is hydrogen or $C_1$-$C_7$ alkyl; and n, which is the average number of oxyalkylene units, has a value within the range of 1 to 100. Preferably, $R^1$ is methyl. Preferably, AO is oxyethylene, oxypropylene, or combinations thereof, more preferably oxyethylene. Preferably, $R^2$ is $R^3$—CH═CH—(CH$_2$)$_7$— or $R^4$O—CO—(CH$_2$)$_7$—CH═CH—(CH$_2$)$_7$—.

In some preferred compositions, n has a value within the range of 0.5 to 5 (also referred to herein as "low-EO" compositions). In other preferred compositions, n has a value within the range of 5 to 15 (also referred to herein as "mid-EO" compositions). In other preferred compositions, n has a value within the range of 15 to 50 (also referred to herein as "high-EO" compositions).

Some specific examples of $C_{10}$, $C_{12}$, $C_{14}$, and $C_{16}$-based alkoxylated fatty esters appear below (where n generally has a value within the range of 1 to 100):

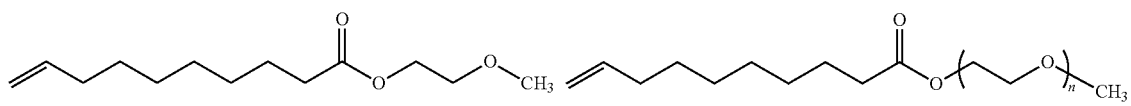

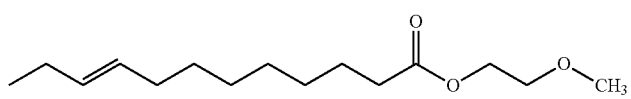

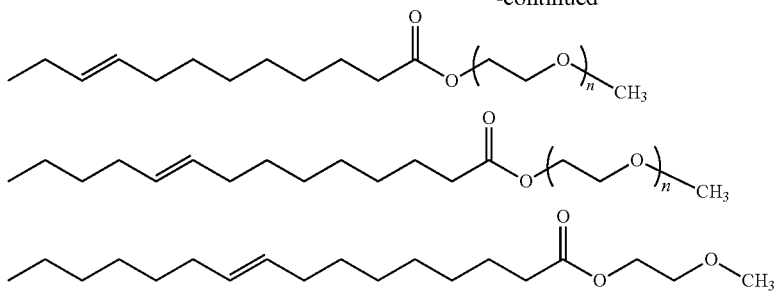

The corresponding sulfonated fatty ester alkoxylates are made by reacting the above-mentioned alkoxylated fatty esters with a sulfonating or sulfitating agent, generally as previously described in Section II.B.1, above.

Exemplary sulfonated or sulfitated products (where n generally has a value within the range of 1 to 100):

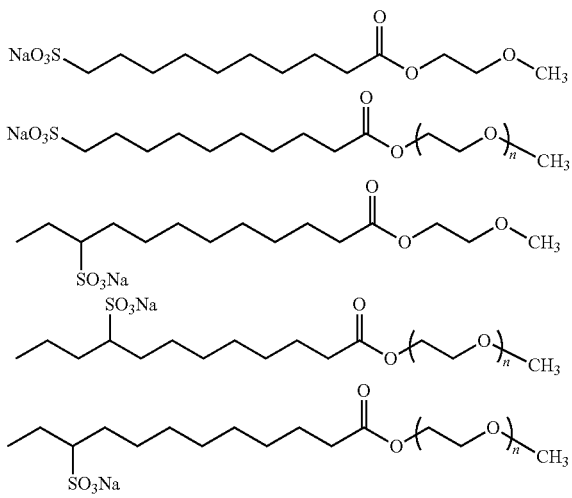

5. Imidazoline Quat Sulfonates

The imidazoline quats (precursors to the imidazoline quat sulfonates) are made by reacting a metathesis-derived $C_{10}$-$C_{17}$ monounsaturated acid, octadecene-1,18-dioic acid, or their ester derivatives with AEEA or DETA, followed by quaternization, as is generally described above in Section I.B.2. The corresponding imidazoline quat sulfonates are made by reacting the above-mentioned imidazoline quats with a sulfonating or sulfitating agent, generally as previously described above in Section II.B.1.

Exemplary imidazoline quat sulfonates:

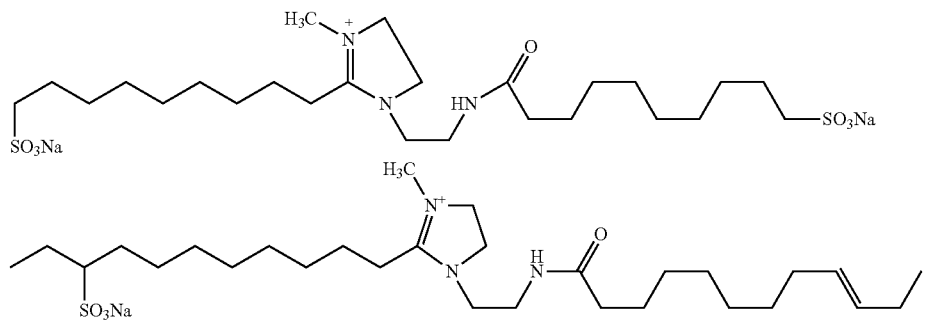

6. Sulfonated Amidoamine Oxides

The amidoamines (precursors to the amidoamine oxides and sulfonated amidoamine oxides) are made by reacting a metathesis-derived $C_{10}$-$C_{17}$ monounsaturated acid, octadecene-1,18-dioic acid, or their ester derivatives with an aminoalkyl-substituted tertiary amine as previously described in Section I.B.1., above.

Oxidation is accomplished by reacting the fatty amidoamine with on oxidant such as hydrogen peroxide, air, ozone, organic hydroperoxides, or the like, to covert a tertiary amine group to an amine oxide functionality according to well-known methods (see *March's Advanced Organic Chemistry*, 5th Ed. (2001), p. 1541 and U.S. Pat. No. 3,494, 924). An exemplary procedure for oxidizing a fatty amidoamine to the corresponding oxide using hydrogen peroxide also appears below.

The corresponding amidoamine oxide sulfonates are made by reacting the above-mentioned amidoamine oxides with a sulfonating or sulfitating agent, generally as previously described above in Section II.B.1.

Examples of suitable $C_{10}$, $C_{12}$, and $C_{14}$-based amidoamine oxides:

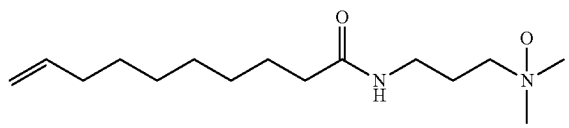

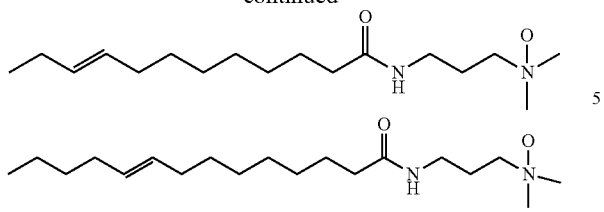

Exemplary sulfonated amidoamine oxides:

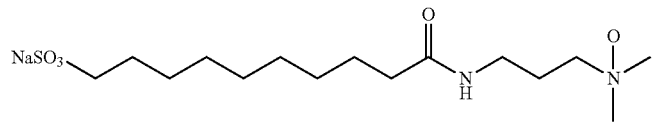

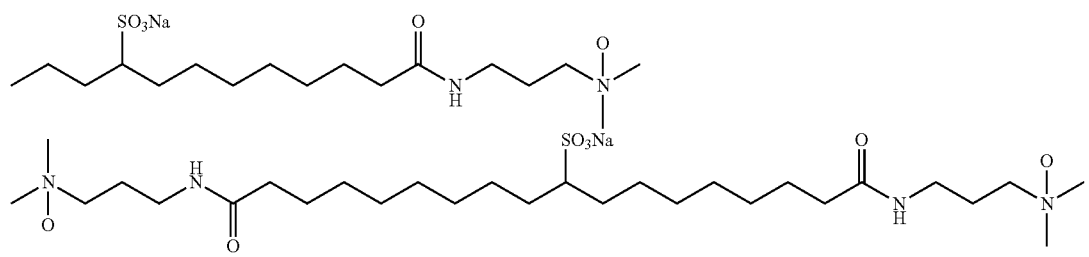

7. Sulfonated Amidoamine Betaines

The amidoamines (precursors to the amidoamine betaines and sulfonated amidoamine betaines) are made by reacting a metathesis-derived $C_{10}$-$C_{17}$ monounsaturated acid, octadecene-1,18-dioic acid, or their ester derivatives with an aminoalkyl-substituted tertiary amine as previously described in Section I.B.1., above.

Suitable amidoamine betaines are made by reacting the fatty amidoamine with an ω-haloalkylcarboxylic acid or alkali metal salt thereof (e.g., sodium monochloroacetate or potassium monochloropropionate) in the presence of a strong base according to well-known methods.

Some amidoamine betaines have the formula:

$R^4(R^3)(R^2)N^+(CH_2)_nNH(CO)R^1$ wherein:
$R^1$ is —$C_9H_{16}$—$R^5$ or —$C_{16}H_{30}$—(CO)NH(CH$_2$)$_n$N$^+$(R$^2$)(R$^3$)R$^4$; each of $R^2$ and $R^3$ is independently substituted or unsubstituted alkyl, aryl, alkenyl, oxyalkylene, or polyoxyalkylene; $R^4$ is $C_2$-$C_4$ alkylene carboxylate; $R^5$ is hydrogen or $C_1$-$C_7$ alkyl; and n=2 to 8. Preferably, $R^1$ is —(CH$_2$)$_7$—CH═CH—$R^5$ or —(CH$_2$)$_7$—CH═CH—(CH$_2$)$_7$—(CO)NH(CH$_2$)$_n$N$^+$(R$^2$)(R$^3$)R$^4$.

Specific examples of $C_{10}$, $C_{12}$, $C_{14}$, and $C_{16}$-based amidoamine betaines appear below:

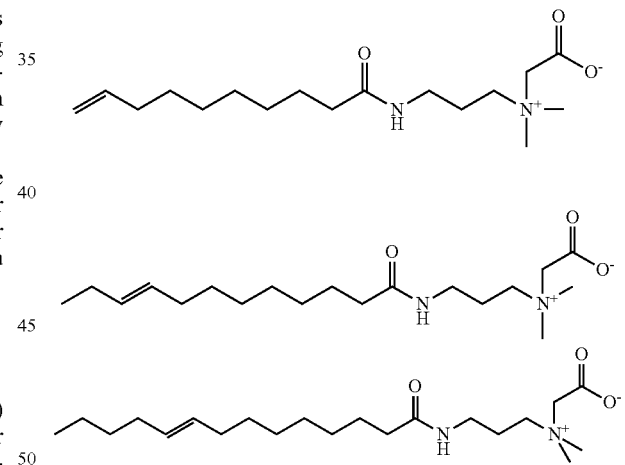

The corresponding amidoamine betaine sulfonates are made by reacting the above-mentioned amidoamine betaines with a sulfonating or sulfitating agent, generally as previously described above in Section II.B.1.

Exemplary sulfonated amidoamine betaines:

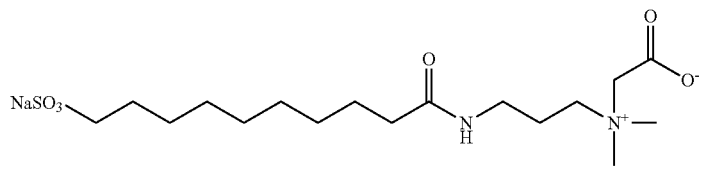

-continued

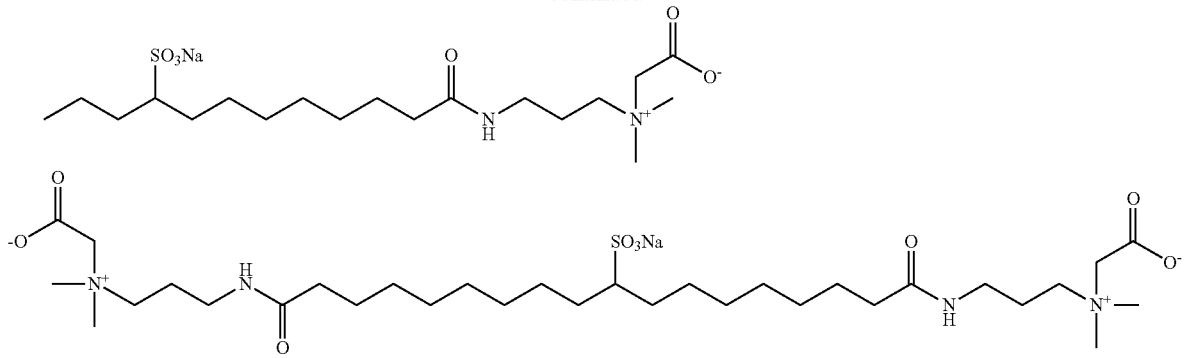

III. Synergy Determination

Blends of the invention exhibit synergy as evidenced by a negative β value or a reduced interfacial tension (IFT) when compared with an expected IFT value calculated from the individual surfactant components.

Interfacial tension is measured by any suitable method. Conveniently, interfacial tension of the individual components and the blends are measured at 0.01% total surfactant actives (diluted in deionized water) at ambient temperature against soybean oil or light mineral oil using a Krüss DSA-20 pendant drop tensiometer. The expected IFT value for a blend is calculated based on ideal mixing (non-synergistic) using the active component in each blend. The equation used is:

$$\text{Expected IFT} = X \cdot \text{IFT}_A + (1-X) \cdot \text{IFT}_B$$

where X is the actives % of Component A, $\text{IFT}_A$ is the IFT of Component A, and $\text{IFT}_B$ is the IFT of Component B.

If the measured IFT for a blend is less than the expected IFT, the blend is synergistic; if the measured IFT for a blend is greater than the expected IFT, the blend is antagonistic.

Synergy can also be evaluated with respect to a blend's beta parameter (β), which can be calculated from the measured critical micelle concentration. Suitable methods for calculating β have been described previously (see, e.g., U.S. Pat. No. 5,360,571, the teachings of which are incorporated herein by reference).

Conveniently, the critical micelle concentration of a blend is measured at dilute concentrations in deionized water with pH adjusted to be within the range of 6 to 7. Critical micelle concentration generally refers to the minimum concentration of surfactant (in mg/L) needed to support micelle formation. The measurement can be performed, for instance, using a Krüss K12 tensiometer at 25° C. Once the critical micelle concentration is measured, the value of β can be found from:

$$\frac{X^2 \ln(\alpha\, C_{12}/XC_1)}{(1-X)^2 \ln[(1-\alpha)C_{12}/(1-X)C_2]} = 1$$

and $$\beta = \frac{\ln(\alpha\, C_{12}/XC_1)}{(1-X^2)}$$

where X is the total mole fraction of Surfactant 1 in the mixed micelles; α is the mole fraction of Surfactant 1 in solution; $C_1$, $C_2$, and $C_{12}$ are the critical micelle concentrations of Surfactant 1, Surfactant 2, and their mixture; and β is the interaction parameter.

A negative value of β indicates synergy, while a positive value of β indicates antagonism, and values close to zero indicate little or no synergy.

Because the blends exhibit synergy, less surfactant is needed (at least in theory) to accomplish a similar task compared with the use of the individual components. Thus, there is an economic incentive to utilize synergistic blends. Traditionally, however, precipitation issues have prevented cationic-anionic surfactant blends from broad applicability (see Background section). The inventive blends, which have at least one component that is metathesis-based, have improved solubility profiles and are less inclined to precipitate from solution, particularly upon dilution with water to commonly used actives levels. Thus, it becomes practical to make a cationic-anionic blend and take advantage of the combined synergy and good solubility.

The surfactant blends are useful for laundry detergents, dish detergents, household or industrial cleaners, personal care products, agricultural products, building materials, oil recovery compositions, emulsion polymers, and other practical applications.

The following examples merely illustrate the invention. Those skilled in the art will recognize many variations that are within the spirit of the invention and scope of the claims.

Feedstock Syntheses

Preparation of Methyl 9-Decenoate ("C10-0") and Methyl 9-Dodecenoate ("C12-0")

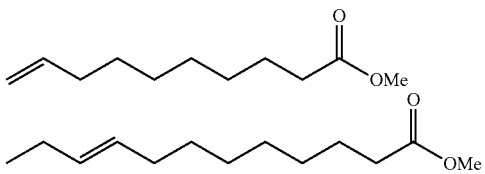

The metathesis procedures of U.S. Pat. Appl. Publ. No. 2011/0113679, the teachings of which are incorporated herein by reference, are used to generate feedstocks C10-0 and C12-0.

Preparation of Dimethyl 9-Octadecene-1,18-dioate ("Mix-0" or "C18-0")

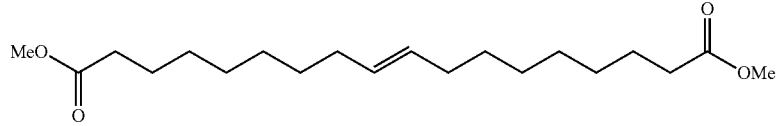 [SMILES: COC(=O)CCCCCCC/C=C/CCCCCCCC(=O)OC]

Eight samples of methyl 9-dodecenoate (10.6 g each, see Table 2) are warmed to 50° C. and degassed with argon for 30 min. A metathesis catalyst ([1,3-bis-(2,4,6-trimethyl phenyl)-2-imidazolidinylidene]dichlororuthenium(3-methyl-2-butenylidene)-(tricyclohexylphosphine), product of Materia) is added to the methyl 9-dodecenoate (amount indicated in Table 2) and vacuum is applied to provide a pressure of <1 mm Hg. The reaction mixture is allowed to self-metathesize for the time reported. Analysis by gas chromatography indicates that dimethyl 9-octadecene-1,18-dioate is produced in the yields reported in Table A. "Mix-0" is an 80:20 trans-/cis- isomer mixture obtained from the reaction mixture. Crystallization provides the all-trans- isomer feed, "C18-0."

TABLE A

Self-Metathesis of Methyl 9-Dodecanoate

| Sample | Catalyst Loading (ppm mol/mol)* | Reaction Time (h) | C18-0 (GC Area %) |
|---|---|---|---|
| A | 100 | 3 | 83.5 |
| B | 50 | 3 | 82.5 |
| C | 25 | 3 | 83.0 |
| D | 10 | 3 | 66.2 |
| E | 15 | 4 | 90.0 |
| F | 13 | 4 | 89.9 |
| G | 10 | 4 | 81.1 |
| H | 5 | 4 | 50.9 |

*ppm mol catalyst/mol methyl 9-dodecenoate

Preparation of Surfactants from Metathesis-Based Feedstocks

C10-25: C10 DMA Amide

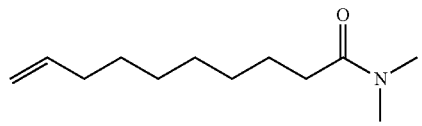

A round-bottom flask is charged with methyl ester feedstock C10-0 (235 g) and the mixture is degassed with nitrogen. Sodium methoxide (5 g of 30% solution in methanol) is added via syringe and the mixture is stirred for 5 min. Dimethylamine (67 g) is slowly added via sub-surface dip tube. After the addition, the mixture is heated to 60° C. and held overnight. The amide, C10-25, is recovered via vacuum distillation (120° C., 20 mm Hg). Yield: 241.2 g (96.3%). Iodine value=128.9 g $I_2$/100 g sample. $^1$H NMR (CDCl$_3$), δ (ppm)=5.8 (CH$_2$=CH—); 4.9 (CH$_2$=CH—); 2.8-3.0 (—C(O)—N(CH$_3$)$_2$); 2.25 (—CH$_2$—C(O)—). Ester content (by $^1$H NMR): 0.54%.

C12-25: C12 DMA Amide

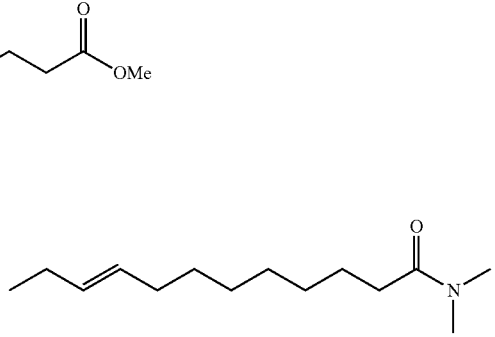

A round-bottom flask is charged with methyl ester C12-0 (900 g) and the feedstock is degassed with nitrogen at 60° C. Sodium methoxide (30 g of 30% solution in methanol) is added via syringe and the mixture is stirred for 5 min. Vacuum is then applied and the reaction vessel sealed. Dimethylamine (200 g) is slowly added via sub-surface dip tube against the static vacuum. After the addition, the remaining vacuum is released with nitrogen, and the mixture is heated to 70° C. for 1 h. The mixture is heated to 80° C., DMA is sparged through the liquid for 2 h, and the mixture is then heated to 90° C. for 1 h. The sparge is stopped, and the reaction is cooled to 75° C. Full vacuum is applied and held for 0.5 h. The vacuum is released, and 50% H$_2$SO$_4$ (16.3 g) and deionized water (200 mL) are added to quench the catalyst. The organic layer is washed with deionized water (2×300 mL, then 1×150 mL) and then 20% brine solution (50 mL). The organic layer is concentrated (full vacuum, 75° C.) and vacuum distilled (pot: 140-150° C.) to isolate amide C12-25. Iodine value: 112.8 g $I_2$/100 g sample; % moisture: 65 ppm. $^1$H NMR (CDCl$_3$), δ (ppm): 5.35 (—CH=CH—); 2.8-3.0 (—C(O)—N(CH$_3$)$_2$; 2.25 (—CH$_2$—C(O)—).

C10-38: C10 Amine

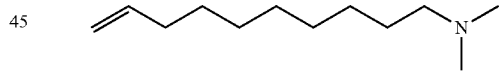

Amide C10-25 (475 g) is slowly added over 3 h to a stirring THF slurry of LiAlH$_4$ (59.4 g) under nitrogen while maintaining the temperature at 11-15° C. The mixture warms to room temperature and stirs overnight. The mixture is chilled in an ice bath, and water (60 g) is added cautiously, followed by 15% aq. NaOH solution (60 g) and then additional water (180 g) is added. The mixture warms to room temperature and is stirred for 1 h. The mixture is filtered, and the filter cake is washed with THF. The filtrates are combined and concentrated. NMR analysis of the crude product indicates that it contains approximately 16% 9-decen-1-ol, a side-product formed during the reduction of the amide. In order to sequester the alcohol, phthalic anhydride is to be added, thus forming the half-ester/acid. The product mixture is heated to 60° C. and phthalic anhydride (57.5 g) is added in portions. NMR analysis of the mixture shows complete consumption of the alcohol, and the mixture is vacuum distilled to isolate C10-38. Amine value: 298.0 mg KOH/g; iodine value: 143.15 g $I_2$/100 g sample; % moisture:

0.02%. $^1$H NMR (CDCl$_3$), δ (ppm): 5.8 (CH$_2$=CH—); 4.9 (CH$_2$=CH—); 3.7 (—CH$_2$—N(CH$_3$)$_2$).

C12-26: C12 Amine

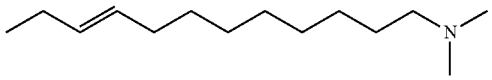

The procedure used to make C10-38 is generally followed with amide C12-25 (620 g) and LiAlH$_4$ (67.8 g). When the reaction is complete, water (68 g) and 15% aq. NaOH solution (68 g) and water (204 g) are used to quench the reaction. After the usual filtration and concentration steps, NMR analysis of the crude product shows approximately 16% 9-dodecen-1-ol to be present. And phthalic anhydride (30 g) is added in order to sequester the alcohol. The mixture is then vacuum distilled to give C12-26. Amine value: 258.1 mg KOH/g sample; iodine value: 120.0 g I$_2$/100 g sample. $^1$H NMR (CDCl$_3$), δ: 5.35 (—CH=CH—); 2.2 (—CH$_2$—N(CH$_3$)$_2$).

C10-17: C10 DMAPA Amide

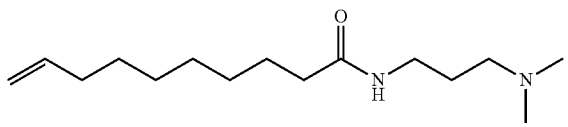 [SMILES: C=CCCCCCCCC(=O)NCCCN(C)C]

A round-bottom flask is charged with methyl ester C10-0 (500 g), DMAPA (331 g), and sodium methoxide/MeOH solution (0.5 wt. % sodium methoxide based on the amount of methyl ester). The contents are heated slowly to 140° C. and held for 6 h. The reaction mixture is vacuum stripped (110° C. to 150° C.). After cooling to room temperature, the product, C10-17, is analyzed. Amine value: 224.1 mg KOH/g; iodine value: 102.6 g I$_2$/100 g sample; titratable amines: 99.94%. $^1$H NMR (CDCl$_3$), δ (ppm): 5.75 (CH$_2$=CH—); 4.9 (CH$_2$=CH—); 3.3 (—C(O)—NH—CH$_2$—); 2.15 (—N(CH$_3$)$_2$).

C12-17: C12 DMAPA Amide

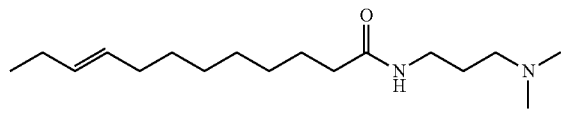 [SMILES: CC/C=C/CCCCCCCC(=O)NCCCN(C)C]

A round-bottom flask is charged with methyl 9-dodecenoate ("C12-0," 670 g). The mixture is stirred mechanically, and DMAPA (387 g) is added. A Dean-Stark trap is fitted to the reactor, and sodium methoxide (30 wt. % solution, 11.2 g) is added. The temperature is raised to 130° C. over 1.5 h, and methanol is collected. After 100 g of distillate is recovered, the temperature is raised to 140° C. and held for 3 h. $^1$H NMR shows complete reaction. The mixture is cooled to room temperature overnight. The mixture is then heated to 110° C. and DMAPA is recovered under vacuum. The temperature is slowly raised to 150° C. over 1.5 h and held at 150° C. for 1 h. The product, amidoamine C12-17, is cooled to room temperature. Amine value: 202.1 mg KOH/g; iodine value: 89.5 g I$_2$/100 g sample; free DMAPA: 0.43%; titratable amines; 100.3%. $^1$H NMR (CDCl$_3$), δ: 5.4 (—CH=CH—); 3.3 (—C(O)—NH—CH$_2$—); 2.2 (—N(CH$_3$)$_2$).

C10-42: C10 Amine DMS Quat

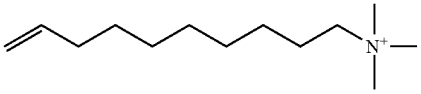

Amine C10-38 (90.1 g) and isopropyl alcohol (50 g) are charged to a flask under nitrogen, and the stirred mixture is warmed to 60° C. Dimethyl sulfate (59.23 g) is added dropwise with air cooling to maintain a reaction temperature of 60-70° C. Additional dimethyl sulfate (0.4 g) is added to ensure full conversion. The mixture is held at 70° C. for 3 h, then at 85° C. for 1 h. On cooling, C10-42 is analyzed: pH: 9.15 (1% in 9:1 IPA/water); free amine: 0.057 meq/g; moisture: 0.05 wt. %; IPA: 24.4 wt. %.

C10-40: C10 Benzyl Quat

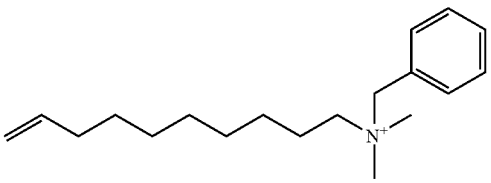 [SMILES: C=CCCCCCCCC[N+](C)(C)Cc1ccccc1]

A flask equipped with a condenser and nitrogen inlet is charged with C10-38 (86.56 g) and methanol (30 g). The mixture is warmed to 80° C. and benzyl chloride (56.37 g) is added. The temperature is raised to 82° C. for 1 h. On cooling, C10-40 is analyzed: pH: 8.6 (1% in 9:1 IPA/water); methanol: 17.5 wt. %; iodine value: 67.37; free amine: 0.065 meq/g; tertiary amine: 0.0169 meq/g; active alkyl quat: 2.645 meq/g.

C12-45: C12 Amine DMS Quat

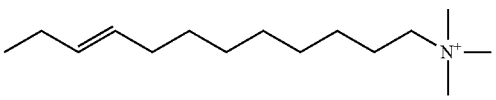 [SMILES: CC/C=C/CCCCCCCC[N+](C)(C)C]

A flask equipped with nitrogen inlet is charged with amine C12-26 (95.5 g), and the contents are warmed to 60° C. Dimethyl sulfate (54.28 g) is added dropwise. The mixture is cooled to maintain a temperature from 65-70° C. During the addition, a precipitate forms, and isopropyl alcohol (26.4 g) is added. The mixture is stirred at 70° C. for 3 h. Additional dimethyl sulfate (0.55 g) is added to ensure a complete conversion, and the mixture is stirred at 70° C. for 3 h, then at 85° C. for 1 h. The product, C12-45, is analyzed: pH: 6.36 (1% in 9:1 IPA/water); free amine: 0.040 meq/g; moisture: 0.4 wt. %; IPA: 11.6 wt. %.

C10-18: C10 DMAPA Quat

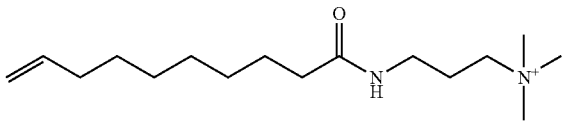 [SMILES: C=CCCCCCCCC(=O)NCCC[N+](C)(C)C]

A flask equipped with condenser and nitrogen inlet is charged with amidoamine C10-17 (151.3 g). After warming to 80° C., dimethyl sulfate (68.38 g) is added dropwise. The temperature is raised to 85° C. and the mixture is stirred for 2 h. Isopropyl alcohol (23.45 g) is added, and the mixture stirs for 1 h. The product, C10-18, is analyzed: IPA: 7.72 wt. %; pH: 8.41 (1% in 9:1 IPA/water); iodine value: 56.8; tertiary amine: 0.020 meq/g; moisture: 1.7 wt. %; quaternary actives: 91.2 wt. %.

C10-19: C10 DMAPA Quat Sulfonate

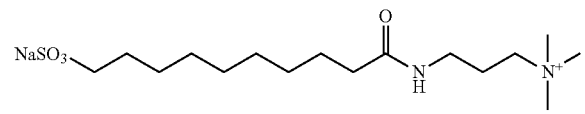

Methyl quat C10-18 (98.30 g) and water (216.3 g) are charged to a round-bottom flask equipped with stir bar, condenser, and thermocouple. The mixture is heated at 80° C. until homogeneous. Sodium metabisulfite ($Na_2S_2O_5$; 23.49 g, 1.03 eq. $NaHSO_3$) is added, and the mixture is held at 80° C. overnight. $^1H$ NMR ($D_2O$) shows ~50% conversion to the sulfitated product. The mixture is held at 80° C. for 48 h and then reanalyzed; there are no significant changes. Sulfur dioxide is bubbled through the mixture, which is then held at 80° C. overnight, but there are still no significant changes in the NMR spectrum. The reaction stirs at room temperature over the weekend. The pH is adjusted to 6.6 and the mixture is heated at 80° C. overnight. NMR analysis shows that olefin peaks have diminished. The pH has dropped to 3 and is adjusted with caustic to 7. After heating for another 24 h, NMR analysis shows no more changes, with ~4-5% olefin remaining. Additional sodium metabisulfite (0.91 g, 0.04 eq. $NaHSO_3$) is added, and the reaction mixture is heated overnight. The $^1H$ NMR spectrum indicates complete conversion to the desired quat sulfonate, C10-19. Analysis shows: moisture: 60.1%; $Na_2SO_4$: 1.93%.

C10-20: C10 DMAPA AO

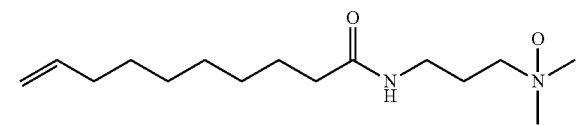

A round-bottom flask is charged with amidoamine C10-17 (162.6 g), water (267 g), and Hamp-Ex 80 (0.5 g). The mixture is heated to 50° C. under nitrogen and several small pieces of dry ice are added. Hydrogen peroxide (35 wt. % aqueous solution, 64.5 g) is added dropwise while keeping the temperature less than 75° C. After completing the $H_2O_2$ addition, the mixture is maintained at 70° C. for 7 h. Peroxide paper test indicates<0.5% residual $H_2O_2$. The mixture is heated for 3 h at 75° C. and then cooled to room temperature to give amine oxide C10-20 in water. The product comprises (by titration): 35.2% amine oxide; 0.85% free amine.

C10-21: C10 DMAPA AO Sulfonate

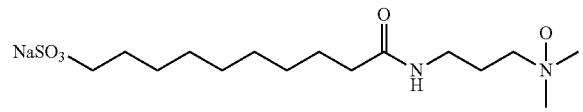

A round-bottom flask equipped with stir bar, condenser, and thermocouple is charged with amine oxide C10-20 (212.4 g, 36.8% solids) and sodium metabisulfite ($Na_2S_2O_5$; 28.09 g, 1.03 eq. $NaHSO_3$), and this mixture is stirred until homogeneous. The solution is heated to 80° C. and the pH is adjusted to 7.5 with $SO_2$ gas. After 30 min., the pH is adjusted again with $SO_2$ to 7.5. After 1 h, the pH is adjusted a third time with $SO_2$ and is then heated at 80° C. overnight. After 16 h, $^1H$ NMR analysis ($D_2O$) indicates a complete reaction. The signal for the amine oxide methyl group had shifted to 2.6 ppm (from 3.1 ppm in the starting material), indicating conversion of amine oxide to sulfitoamine. Sodium hydroxide (5.46 g, 0.2 eq.) is added to hydrolyze the sulfitoamine and the mixture is heated at 80° C. overnight. After 16 h, $^1H$ NMR analysis indicates that the amine methyl signal has shifted to 2.2 ppm, indicating hydrolysis of sulfitoamine to the corresponding amine. The mixture is cooled to 50° C. and the pH is adjusted from 10.1 to 8.3 by adding dry ice. Hydrogen peroxide (28.43 g, 1.02 eq.) is added dropwise, maintaining the reaction temperature below 70° C. The mixture is maintained at 70° C. for 16 h. The mixture is cooled to provide sulfonate C10-21 as an aqueous solution. Analysis by $^1H$ NMR ($D_2O$) confirms formation of the amine oxide sulfonate, based appearance of the $N(CH_3)_2$ at 3.2 ppm, which matches up well with the $N(CH_3)_2$ in the starting amine oxide, and a new signal at 2.7 ppm corresponding to the protons adjacent to the sulfonate group (—$CH_2SO_3Na$).

C12-18: C12 DMAPA Quat

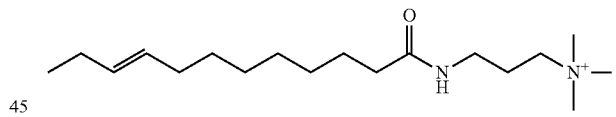

A flask equipped with condenser and nitrogen inlet is charged with amidoamine C12-17 (155.8 g), which is warmed to 80° C. Dimethyl sulfate (68.38 g) is added dropwise. The reaction temperature is raised to 85° C. and held for 1 h, then to 95° C. for 3 h. Isopropyl alcohol (24.9 g) is added, and the mixture stirs for 1 h. Analysis of the quat product, C12-18, shows: IPA: 8.9 wt. %; iodine value: 53.95; pH: 8.07 (1% in 9:1 IPA/water); moisture: 0.6 wt. %.

MIX-26: C18 DiDMAPA Amide (80% trans, 20% cis)

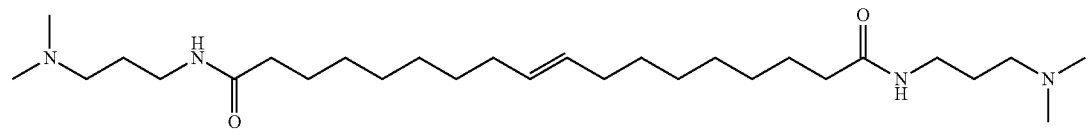

Dimethyl ester C18-0 (824.3 g), DMAPA (519.5 g), and sodium methoxide solution (2.4 wt. % NaOMe based on methyl ester) are heated slowly to 140° C. and held for several hours. A subsurface nitrogen sparge is utilized at the end to facilitate the removal of methanol. The temperature is reduced to 100° C., and the contents are vacuum stripped. A solution made from deionized water (1.0 L) and 50% $H_2SO_4$ (11 g) is added slowly to the molten reaction product. The mixture cools, and the pasty solids are isolated by filtration. The solids are washed with deionized water, and the filtrate is extracted with chloroform (2×250 mL). The chloroform extracts are concentrated, and the resulting yellow oil is identified as the cis-enriched product by $^1$H NMR. The yellow oil is redissolved in $CHCl_3$, filtered through silica, and combined with the pasty solids. Additional $CHCl_3$ (100 mL) is added to the contents, and the mixture is swirled on a rotary evaporator at 70° C. until homogeneous. Vacuum is applied, and the $CHCl_3$ is removed, followed by water. Evaporation is discontinued when the product remains a solid at 98° C. The cooled product, Mix-26, is analyzed: amine value: 229.1 mg KOH/g sample; free DMAPA: 0.08%; moisture: 0.09%; total alkalinity: 4.08 meq/g. $^1$H NMR ($CDCl_3$), δ (ppm)=5.3 (—CH=CH—); 3.25 (—C(O)—NH—$CH_2$—); 2.2 (—N($CH_3$)$_2$). $^{13}$C NMR ($CDCl_3$), δ (ppm)=130 (trans —CH=CH—); 129.5 (cis, —CH=CH—). Product ratio: 79.3% trans, 20.7% cis.

MIX-27: C18 DiDMAPA DiQuat (80:20 trans-/cis-)

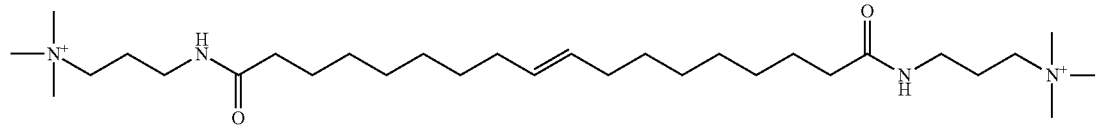

A flask equipped with condenser and nitrogen inlet is charged with diamide Mix-26 (157.3 g), which is warmed to 80° C. Dimethyl sulfate (68.38 g) is added dropwise. The reaction temperature is raised to 85° C. and the mixture is stirred for 2 h. Isopropyl alcohol (23.45 g) is added, and the mixture stirs for 1 h. The diquat product, Mix-27, is analyzed: IPA: 7.72 wt. %; pH: 8.41 (1% in 9:1 IPA/water); iodine value: 56.76; tertiary amine: 0.020 meq/g; moisture: 1.7 wt. %; quaternary actives: 91.2 wt. %.

C10-1: C10 Sulfonate

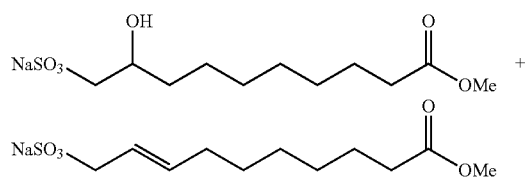

In a batch reactor maintained at 20° C. under a nitrogen flow (2 L/min.), methyl decenoate (106.7 g, 0.58 mol) is added to methylene chloride (100 mL). Sulfur trioxide (46.1 g, 0.58 mol) is evaporated over 30 min. via a 140° C. flash-pot and is bubbled through the reactor using the nitrogen stream. The addition rate of $SO_3$ is adjusted to keep the reaction temperature at or below 35° C. At the end of the addition, the reaction mixture is maintained for an additional 5 min. and the mixture is then concentrated under vacuum. The acid product is then digested for 1 h at 50° C. Methanol (7.5 g) is added to the acid (~150 g), and the solution is heated to 65° C. for 1 h. The mixture is cooled to 0° C., and a solution prepared from 50% aqueous NaOH (16.48 g) and water (142.6 g) is slowly added. When the addition is complete, the pH is about 1.5. Additional 50% aq. NaOH solution (4.2 g) is added to adjust the pH to about 7. The mixture is heated to 85° C. while monitoring pH. The pH is kept between 5 and 7 by adding more 50% aq. NaOH. The stirred solution is heated at 85° C. for a total of 8 h under a nitrogen purge to remove methanol and completely hydrolyze sultones. The resulting product ("C10-1") is a mixture that includes an alkenesulfonate and a hydroxyalkane sulfonate. Moisture: 46.7 wt. %; sodium sulfate: 0.27 wt. %.

C12-1: C12 Sulfonate

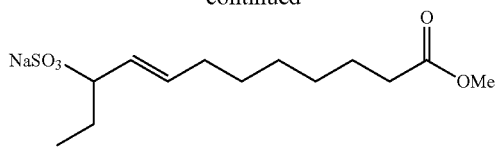

-continued

C12-1 is synthesized in a manner similar to C10-1 using C12-0 (106.7 g, 0.579 mol), methylene chloride (100 mL), and sulfur trioxide (46.1 g, 0.575 mol). Digestion is carried out for 1 h at 65° C. Methanol (7.7 g) is added, and the mixture is warmed to 65° C. for 1 h. The acid is neutralized at 0° C. using aqueous sodium hydroxide (20.3 g of 50% aq. NaOH in 141.6 g of water). Hydrolysis is carried out at 85° C. until determined complete by $^1$H NMR. The pH is maintained between 5-7 with further additions of 50% NaOH (aq). After the hydrolysis, a material found to be the starting methyl ester oils out of solution and forms a small layer on top of the neutralized material. The oil layer is removed and the aqueous layer is analyzed. $^1$H NMR data supports the proposed composition. Moisture: 47.1 wt. %; pH: 8.58 (1% in 9:1 IPA/water); sodium sulfate: 0.52 wt. %; unsulfonated matter: 2.05 wt. %; methanol: 0.53 wt. %.

C10-36: C10 Fatty Acid

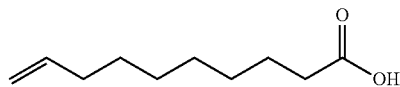

Methyl ester C10-0 (390.2 g) is charged to a round-bottom flask equipped with an overhead stirrer. After warming to 70° C., a mixture of KOH in glycerol (16% KOH, 523 g) is added. The mixture is warmed to 100° C. and more solid KOH (35.1 g) is added. The mixture stirs for ~17 h. Gas chromatography shows ~94% conversion to the free fatty acid. More solid KOH (10 g) is added, and the mixture stirs at 100° C. for 4 h. Conversion by GC is now >97%. The mixture stirs at 100° C. for another 4 h and then cools to 80° C. Water (400 mL) and 30% aq. H₂SO₄ (500 mL) are added. The mixture stirs at 80° C. for ~1 h. The layers are separated, and the aqueous layer is removed. More water (500 mL) is added, and the mixture is again heated to 80° C. with stirring for 30 min. The layers are again separated, and the aqueous phase is discarded. The washing process (with 500 mL of water) is repeated two more times. The resulting free fatty acid, C10-36, is stripped under vacuum (80° C., 2 h) and is thereafter used without further purification. Yield: 357 g. ¹H NMR results are consistent with the proposed structure. Moisture: 315 ppm.

C10-6: C10 DMEA Ester

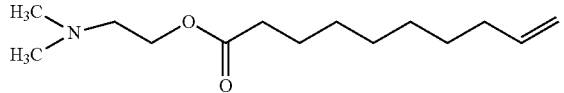 [SMILES: C=CCCCCCCCC(=O)OCCN(C)C]

Fatty acid C10-36 (153.7 g, 0.890 mol) and N,N-dimethylethanolamine (142.7 g, 1.60 mol) are charged to a flask equipped with heating mantle, temperature controller, mechanical agitator, nitrogen sparge, five-plate Oldershaw column, and condenser. The mixture is gradually heated to 180° C. while the overhead distillate temperature is kept below 105° C. After the reaction mixture temperature reaches 180° C., it is held at this temperature overnight. Free fatty acid content by ¹H NMR: 5% (essentially complete). The mixture is cooled to 90° C. and the column, condenser, and nitrogen sparge are removed. Vacuum is applied in increments to 20 mm Hg over ~1 h, held at held at 20 mm Hg for 0.5 h, then improved to full vacuum for 1.5 h. The esteramine product, C10-6, has an unreacted dimethylethanolamine value of 0.41%. Purity is confirmed by a satisfactory ¹H NMR spectrum.

C10-7: C10 DMEA Ester Quat

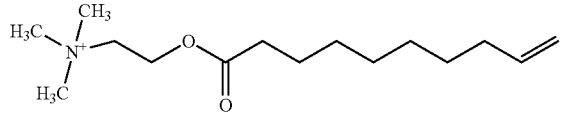 [SMILES: C=CCCCCCCCC(=O)OCC[N+](C)(C)C]

Esteramine C10-6 (98.9 g) and isopropyl alcohol (26.2 g) are charged to a round-bottom flask equipped with a reflux condenser, thermocouple/heating mantle, and nitrogen inlet. The sample is heated to 65° C. Dimethyl sulfate (49.6 g) is added dropwise via an addition funnel. Temperature is kept at or below 70° C. After the DMS is added, the temperature is increased to 70° C. and stirred for 3 h. The reaction is considered complete, as the perchloric acid titration (PAT) value indicates <2% quaternizable amine remaining based on the original PAT value of the esteramine. The reaction mixture is also heated at 80-85° C. for 1 h to ensure complete DMS removal; contents are also tested with a Dräger apparatus for residual DMS.

C10-8: C10 Ethoxylated Fatty Acid Methyl Ester ("eFAME")

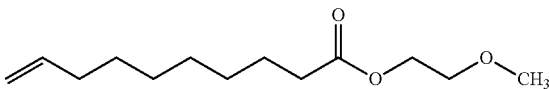 [SMILES: C=CCCCCCCCC(=O)OCCOC]

C10-36 fatty acid (196.7 g, 1.117 mol) is charged to a round-bottom flask equipped with an overhead stirrer, Dean-Stark trap, reflux condenser, thermocouple, heating mantle, and temperature controller. 2-Methoxyethanol (170.0 g) and toluene (500 mL) are added. The mixture is heated to 124° C. while p-toluenesulfonic acid (1.7 g) is added. Water of reaction begins to collect when the target temperature is reached. Heating continues for 4.5 h, and conversion to the eFAME (by ¹H NMR) is 96%. (Signals for the hydrogens alpha to the carbonyl are used to determine degree of conversion.) The sample is stripped to remove toluene and excess 2-methoxyethanol. Residual toluene is removed by stirring at 150° C. under vacuum (1-5 mm Hg) with a low nitrogen sparge.

C10-29: C10 eFAME Sulfonate

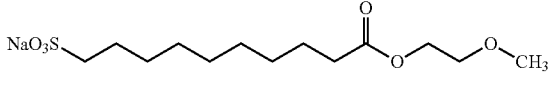

A round-bottom flask equipped with stir bar, thermocouple, heating mantle, temperature controller, and pH probe is charged with sodium bisulfite (as Na₂S₂O₅, 27.5 g) and deionized water (120.0 g). The pH is adjusted to 6.6 by adding sodium hydroxide (11.6 g). The mixture is heated to 75° C. Isopropyl alcohol (20.0 g) is added, followed by t-butylperoxybenzoate ("TBB," 50 µL, added by syringe). After 0.5 h, olefin C10-8 (64.3 g) is slowly added, followed by the remaining TBB (225 µL). The pH is kept at 7.0±0.1 with a low SO₂ sparge. After 16 h, ¹H NMR in D₂O shows olefin peaks. The pH drifts to 8.8 and is adjusted down to 6.8 with a low SO₂ sparge, and more isopropyl alcohol (40 mL) is added to aid with solubility. After another 5 h, pH again drifts upward and is adjusted to 6.8 with a low SO₂ sparge. After another 1.5 h, ¹H NMR indicates complete reaction.

C10-12: C10 DETA Amide

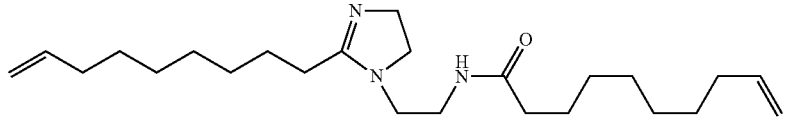

A round-bottom flask is charged with fatty acid C10-36 (310 g) and the feedstock is degassed with nitrogen. Diethylenetriamine ("DETA," 62.6 g) is added and the mixture is heated from 130° C. to 170° C. over 4 h and stirred (170 rpm) under a flow of nitrogen (175 mL/min.). After 18 h, titration reveals 0.097 meq/g of free fatty acid. The temperature is increased to 200° C. for 4 h. Titration indicates 96% ring closure to form C10-12.

C10-13: C10 DETA Quat

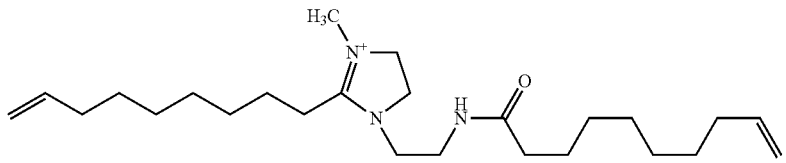 [SMILES: C=CCCCCCCCC(=O)NCCN1CC[N+](C)=C1CCCCCCCC=C]

A round-bottom flask is charged with imidazoline C10-12 (202.1 g), which is degassed with nitrogen and heated to 75° C. Dimethyl sulfate ("DMS," 60.6 g) is added via addition funnel with cooling to keep the reaction temperature at ~80° C. After the DMS addition is complete, the mixture is held at 80° C. for 1 h. Free amine (by perchloric acid titration): 0.067 meq/g. Isopropyl alcohol (IPA) (13.9 g) is added, and the mixture is heated to 85° C. for 1 h to destroy any unreacted DMS.

C10-32: C10 UFA SLA

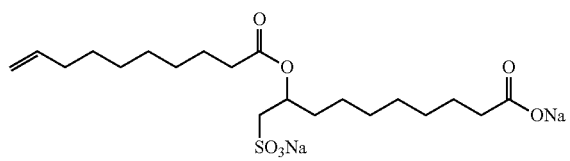

The procedure used to prepare C10-1 is generally followed with methylene chloride (100 mL) and sulfur trioxide (51.6 g, 0.644 mol), except that fatty acid C10-36 (109.6 g, 0.644 mol) is used instead of methyl ester C10-0. During SO$_3$ addition, more methylene chloride (100 mL) is added to reduce viscosity. The acid is neutralized with water (151.0 g) followed by 50% aq. NaOH (41.69 g). Hydrolysis is carried out at 85° C. and pH is maintained with additional 50% NaOH (aq) additions. $^1$H NMR of the sulfo-estolide product, C10-32, supports the proposed structure. Analysis shows: pH: 5.25 (as is); moisture: 51.6 wt. %; sodium sulfate: 0.51 wt. %; unsulfonated matter: 0.79 wt. %.

C18-1: C18 Sulfonate

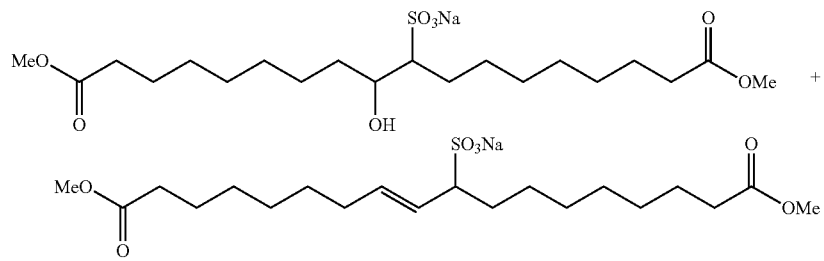

The procedure used to synthesize C10-1 is generally followed using C18-0 (125.8 g, 0.370 mol), methylene chloride (100 mL), and sulfur trioxide (30.4 g, 0.380 mol). Digestion is carried out for 1 h at 65° C. Methanol (7.24 g) is added, and the mixture is warmed to 65° C. for 1 h. The acid is neutralized at 0° C. using aqueous sodium hydroxide (a mixture of 19.2 g of 50% NaOH and 107 g of water). Hydrolysis is carried out at 85° C. until $^1$H NMR shows complete conversion. The pH is maintained between 5-7 with further additions of 50% NaOH (aq). After the hydrolysis, a small layer of oil, found to be starting methyl ester, forms on the surface and is removed. $^1$H NMR results supported the proposed composition for C18-1. Analysis shows: pH: 5.56 (1% in 9:1 IPA/water); moisture: 30.7 wt. %; sodium sulfate: 1.59 wt. %; unsulfonated matter: 5.62 wt. %.

C10-26: C10 DMA Sulfonate

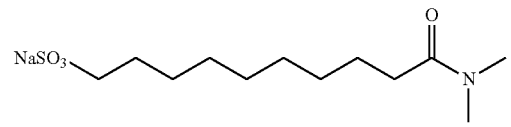

Sulfur trioxide (23.6 g) is added dropwise to unsaturated amide C10-25 (48.6 g) in a vaporizer at a rate effective to maintain the reaction temperature between 35-40° C. Initial fuming in the reactor headspace is minimal. About halfway through the SO$_3$ addition, the reaction product becomes too viscous to stir adequately. The reactor is fitted with a dry ice/acetone trap and the product is diluted with methylene chloride (50 mL) to aid agitation. The reaction temperature is maintained between 20° C.-25° C. Additional methylene chloride (20 mL) is added during the SO$_3$ addition to maintain fluidity. At the end of the addition, the reactor is purged with nitrogen for 5 min. Total addition time: 45 min. The yellow-brown product (104.76 g) is transferred to a round-bottom flask, and solvent is removed under vacuum (~40° C., 2 h). The resulting sulfonic acid is digested at 45° C. for 30 min. Yield: 71.4 g.

Aqueous sodium hydroxide (75 g of 10.7% solution) is added to the dried sulfonic acid. The pH is adjusted as necessary. Once dissolved, the mixture is transferred to a flask equipped with mechanical stirring. Water (78.4 g) and aqueous NaOH (24.6 g of 50% solution) are added. The mixture is heated to 95° C. overnight, maintaining pH=7 with 50% aq. NaOH solution, and then cooled.

Preparation of Surfactant Blends

All of the surfactant blends tested are prepared at the designated molar ratios without any pH adjustment. Dilutions are made using deionized water to the desired actives level. Actives amounts are wt. % unless indicated otherwise. Appearances are reported at ambient temperature for samples prepared within the last 24 h.

Interfacial tension (IFT) of all the individual components and their blends is measured at a given % active against light mineral oil at ambient temperature using a Kruss DSA-20 pendent drop tensiometer.

The critical micelle concentration (CMC) of a blend is measured at a diluted concentration in deionized water with pH adjusted to 6-7. The measurement is done at 25° C. using a Kruss K100 tensiometer. The synergy of the blends, indicated by the beta parameter, is calculated based on the CMC data using the equation, $$\beta = [\ln(\alpha A_{12}/XA_1)]/(1-X)^2$$

in which $\alpha$ is the mole fraction of the anionic surfactant in solution, X is the mole fraction of the anionic surfactant in mixed micelles, $A_1$ is the critical micelle concentration of the anionic surfactant, and $A_{12}$ is the critical micelle concentration of the blend.

Surfactant Identification Table

|  | % actives | EW | generic name |
|---|---|---|---|
| Commercial Product[1] |  |  |  |
| Stepanol ® WA-Extra | 29.2-29.4 | 302 | sodium lauryl sulfate |
| Ammonyx ® Cetac 30 | 29.4 | 320 | cetrimonium chloride |
| BTC ® 2125M | 51.1 | 377 | myristylalkonium chloride + quaternium 14 |
| Alpha-Step ® PC-48 | 37 | 338 | sodium methyl 2-sulfolaurate + disodium 2-sulfolaurate |
| Stepanate ® SXS | 40.6 | 208 | sodium xylene sulfonate |
| Bio-Terge ® PAS-8S | 40.5 | 242 | sodium octane sulfonate |
| Bio-Terge ® AS-40 | 39.3 | 315 | sodium C14-C16 olefin sulfonate |
| Stepanquat ® 1010-80 | 81.9 | 362 | dodecyl dimethylammonium chloride |
| Inventive Surfactant |  |  |  |
| C10-1 | 53.0 | 295 | C10 fatty ester sulfonate |
| C10-7 | 86.8 | 368 | C10 DMEA ester quat |
| C10-13 | 86.9 |  | C10 DETA quat |
| C10-19 | 34.6 | 485 | C10 DMAPA quat sulfonate |
| C10-21 | 47.1 | 376 | C10 DMAPA amine oxide sulfonate |
| C10-26 | 40.1 | 301 | C10 fatty amide sulfonate |
| C10-29 | 45.8 | 332 | C10 ethoxylated fatty methyl ester |
| C10-40 | 82.0 | 310 | C10 fatty amine benzyl quat |
| C12-1 | 52.4 | 323 | C12 fatty ester sulfonate |

[1]All products of Stepan Company.

TABLE 1

Metathesis-based Cationic Surfactant (C10-42) + Anionic Surfactants

|  | Sample | | |
|---|---|---|---|
|  | C10-42 | C10-1 | Stepanol ® WA-Extra |
| Type | cationic | anionic | anionic |
| Name | C10 DMS quat | C10 sulfonate | sodium lauryl sulfate |
| Metathesis-based? | Y | Y | N |
| IFT (0.1% actives) | 42.0 | 47.1 | 7.8 |
| C10-42:anionic (molar) |  | 1:1 | 1:1 |
| Total actives of blend, % |  | 22.8 | 42.1 |
| Appearance, neat |  | clear liquid | 2 layers |
| Appearance, 1.0% |  | clear liquid | hazy liquid |
| Appearance, 0.1% |  | clear liquid | slightly hazy liquid |
| Calculated IFT (no synergy) |  | 44.5 | 25.1 |
| Measured IFT (0.1% actives) |  | 18.8 | 1.9 |
| Synergy? |  | Y | Y |
| Solubility |  | good | fair-poor |

TABLE 2

Metathesis-based Cationic Surfactant (Mix-27) + Anionic Surfactants

|  | Sample | | |
|---|---|---|---|
|  | Mix-27 | C10-1 | Stepanol ® WA-Extra |
| Type | cationic | anionic | anionic |
| Name | C18 diDMAPA diquat | C10 sulfonate | sodium lauryl sulfate |
| Metathesis-based? | Y | Y | N |
| IFT (0.1% actives) |  | 47.1 | 7.8 |
| Mix-27:anionic (molar) |  | 1:2 | 1:2 |
| Total actives of blend, % |  | 46.0 | 45.9 |
| Appearance, neat |  | clear liquid | clear liquid |
| Appearance, 1.0% |  | clear liquid | hazy liquid |
| Appearance, 0.1% |  | clear liquid | hazy liquid |
| Calculated IFT (no synergy) |  | 35.3 | 18.0 |

TABLE 2-continued

Metathesis-based Cationic Surfactant (Mix-27) + Anionic Surfactants

| | Sample | | |
|---|---|---|---|
| | Mix-27 | C10-1 | Stepanol ® WA-Extra |
| Measured IFT (0.1% actives) | | 11.1 | 4.4 |
| Synergy? | | Y | Y |
| Solubility | | good-fair | good-fair |

As shown in Tables 1 and 2, combinations of a metathesis-based cationic surfactant comprising a quaternized derivative, here a fatty amine quat (C10-42) or a fatty amidoamine quat (Mix-27), demonstrate synergy with anionic surfactants. The anionic surfactant may or may not be metathesis-based. In addition to the reduction in IFT versus the calculated value with no synergy, the blends demonstrate acceptable to good solubility, particularly at the 0.1 and 1.0% actives levels commonly used in practical applications.

TABLE 3

Metathesis-based Anionic Surfactant (C10-1) + Cationic Surfactants

| | Sample | | |
|---|---|---|---|
| | C10-1 | BTC ® 2125M | Ammonyx ® Cetac 30 |
| Type | anionic | cationic | cationic |
| Name | C10 sulfonate | myristylalkonium Cl + quaternium 14 | cetrimonium Cl |
| Metathesis-based? | Y | N | N |
| IFT (0.1% actives) | 47.1 | 6.4 | 9.3 |
| C10-1:cationic (molar) | | 1:1 | 1:1 |
| Total actives of blend, % | | 51.9 | 37.4 |
| Appearance, neat | | 2 layers | clear liquid |
| Appearance, 1.0% | | opaque liquid | clear liquid |
| Appearance, 0.1% | | sl. hazy liquid | clear liquid |
| Calculated IFT (no synergy) | | 25.8 | 27.4 |
| Measured IFT (0.1% actives) | | 0.09 | 2.6 |
| Synergy? | | Y+ | Y |
| Solubility | | good-fair | good |

TABLE 4

Metathesis-based Anionic Surfactant (C10-26) + Cationic Surfactants

| | Sample | | | |
|---|---|---|---|---|
| | C10-26 | BTC ® 2125M | Ammonyx ® Cetac 30 | C10-42 |
| Type | anionic | cationic | cationic | cationic |
| Name | C10 amide sulfonate | myristylalkonium Cl + quaternium 14 | cetrimonium Cl | C10 DMS quat |
| Metathesis-based? | Y | N | N | Y |
| IFT (0.1% actives) | 12.5 | 6.4 | 9.3 | 42.0 |
| C10-26:cationic (molar) | | 1:1 | 1:1 | 1:1 |
| Total actives of blend, % | | 47.9 | 57.3 | 55.6 |
| Appearance, neat | | 2 layers | clear liquid | clear liquid |
| Appearance, 1.0% | | clear liquid | clear liquid | hazy liquid |
| Appearance, 0.1% | | clear liquid | clear liquid | clear liquid |
| Calculated IFT (no synergy) | | 9.1 | 10.9 | 27.4 |
| Measured IFT (0.1% actives) | | 3.7 | 6.2 | 17.6 |
| Synergy? | | Y | Y | Y |
| Solubility | | good-fair | good | good |

TABLE 5

Metathesis-based Anionic Surfactant (C10-32) + Cationic Surfactants

| | Sample | | |
|---|---|---|---|
| | C10-32 | C10-42 | Ammonyx ® Cetac 30 |
| Type | anionic | cationic | cationic |
| Name | C10 sulfoestolide | C10 DMS quat | cetrimonium Cl |
| Metathesis-based? | Y | Y | N |
| IFT (0.1% actives) | 25.9 | 42.0 | 9.3 |
| C10-32:cationic (molar) | | 1:1 | 1:1 |
| Total actives of blend, % | | 56.8 | 38.6 |
| Appearance, neat | | clear liquid | clear liquid |
| Appearance, 1.0% | | hazy liquid | clear liquid |
| Appearance, 0.1% | | clear liquid | clear liquid |
| Calculated IFT (no synergy) | | 32.4 | 19.2 |
| Measured IFT (0.1% actives) | | 10.0 | 2.1 |
| Synergy? | | Y | Y |
| Solubility | | good-fair | good |

TABLE 6

Metathesis-based Anionic Surfactant (C18-1) + Cationic Surfactants

| | Sample | | |
|---|---|---|---|
| | C18-1 | C10-42 | Ammonyx ® Cetac 30 |
| Type | anionic | cationic | cationic |
| Name | C18 sulfonate | C10 DMS quat | cetrimonium Cl |
| Metathesis-based? | Y | Y | N |
| IFT (0.1% actives) | 11.7 | 42.0 | 9.3 |
| C18-1:cationic (molar) | | 1:1 | 1:1 |
| Total actives of blend, % | | 71.9 | 43.8 |
| Appearance, neat | | hazy liquid | clear liquid |
| Appearance, 1.0% | | hazy liquid | hazy liquid |
| Appearance, 0.1% | | clear liquid | hazy liquid |
| Calculated IFT (no synergy) | | 24.1 | 10.7 |
| Measured IFT (0.1% actives) | | 12.8 | 2.9 |
| Synergy? | | Y | Y |
| Solubility | | fair | fair |

The results in Tables 3-6 demonstrate the use of a metathesis-based anionic surfactant comprising a sulfonated derivative with a cationic surfactant. The sulfonated derivatives include sulfonated esters, amide sulfonates, and sulfoestolides. Based on the IFT data, each of the blends demonstrates synergy. The cationic surfactant may or may not be metathesis-based.

In Tables 7-9 (below), blends made from metathesis-based cationic surfactants and an anionic surfactant (Stepanol® WA-Extra, sodium laurel sulfate, "SLS") are compared with blends made using SLS and a saturated analog of the metathesis-based cationic surfactant. The metathesis-based cationic surfactants are principally monounsaturated materials. All of the blends in these tables are synergistic, as indicated by the large negative values of β. However, the solubility profiles of blends containing the unsaturated materials (C10-18, C12-18, and C12-45) are generally more favorable, particularly for the C12 products. The results suggest that monounsaturation may provide advantages to formulators that need to ensure that actives will remain dissolved (and not precipitate) when combinations of anionic and cationic surfactants are used. The solubility advantages should allow formulators to take advantage of synergy in cationic/anionic surfactant blends by using less of the blend to achieve a desired reduction in surface tension, improvement in cleaning, or other related properties.

TABLE 7

Blends of SLS and Metathesis-Based Cationic Surfactants: Effect of Unsaturation

| | Monounsaturated C10 DMAPA quat (C10-18) | | | | Saturated analog | | | |
|---|---|---|---|---|---|---|---|---|
| SLS/Quat | Appearance | | | | Appearance | | | |
| (molar) | concentrate | 0.2% actives | 0.01% actives | Beta | concentrate | 0.2% actives | 0.01% actives | Beta |
| 1:0 | clear | clear | clear | | clear | clear | clear | |
| 4:1 | clear | clear | clear | -3.9 | viscous | clear | clear | -6.8 |
| 2:1 | 2 layers | viscoelastic | clear | -5.0 | 2 layers | viscoelastic | clear | -7.9 |
| 1:1 | clear | hazy | clear | -7.0 | clear | hazy | clear | -8.3 |
| 1:2 | clear gel | clear | clear | -8.7 | clear | slightly hazy | clear | -11.8 |
| 1:4 | clear gel | hazy | clear | -10.9 | clear | clear | clear | -13.3 |
| 0:1 | solid | clear | clear | | solid | clear | clear | |

All samples are liquid unless noted otherwise.
SLS = Stepanol ® WA-Extra (sodium lauryl sulfate).

TABLE 8

Blends of SLS and Metathesis-Based Cationic Surfactants: Effect of Unsaturation

| SLS/Quat (molar) | Monounsaturated C12 DMAPA quat (C12-18) | | | | Saturated analog | | | |
|---|---|---|---|---|---|---|---|---|
| | Appearance | | | | Appearance | | | |
| | concentrate | 0.2% actives | 0.01% actives | Beta | concentrate | 0.2% actives | 0.01% actives | Beta |
| 1:0 | clear | clear | clear | | clear | clear | clear | |
| 4:1 | clear | clear | clear | −8.4 | clear | clear | clear | −8.4 |
| 2:1 | hazy, viscous | slightly hazy | clear | −10.9 | hazy, viscous | clear | clear | −10.1 |
| 1:1 | hazy, viscous | cloudy | hazy | −12.0 | hazy, viscous | cloudy | hazy | −8.2 |
| 1:2 | clear | slightly hazy | clear | −13.3 | top hazy, bottom clear | slightly hazy | hazy | −12.7 |
| 1:4 | clear | clear | slightly hazy | −16.0 | clear gel | clear | hazy | −14.4 |
| 0:1 | solid | clear | clear | | solid | clear | clear | |

All samples are liquid unless noted otherwise.
SLS = Stepanol ® WA-Extra (sodium lauryl sulfate).

TABLE 9

Blends of SLS and Metathesis-Based Cationic Surfactants: Effect of Unsaturation

| SLS/Quat (molar) | Monounsaturated C12 DMA quat (C12-45) | | | | Saturated analog | | | |
|---|---|---|---|---|---|---|---|---|
| | Appearance | | | | Appearance | | | |
| | concentrate | 0.2% actives | 0.01% actives | Beta | concentrate | 0.2% actives | 0.01% actives | Beta |
| 1:0 | | | | | | | | |
| 4:1 | hazy | slightly hazy | clear | −9.3 | 2 layers | hazy | almost clear | −10.5 |
| 2:1 | opaque | hazy | almost clear | −11.0 | 2 layers | hazy | hazy | −11.2 |
| 1:1 | lamellar | hazy | almost clear | −14.1 | paste | hazy | almost clear | −13.8 |
| 1:2 | 2 layers | hazy | hazy | −15.0 | 2 layers | hazy | hazy | −14.2 |
| 1:4 | clear | slightly hazy | clear | −18.5 | 2 layers | hazy | almost clear | −19.1 |
| 0:1 | | | | | | | | |

All samples are liquid unless noted otherwise.
SLS = Stepanol ® WA-Extra (sodium lauryl sulfate).

TABLE 10

Metathesis-based Anionic Surfactant (C10-1) in Combination with Ammonyx ® Cetac 30 (Cationic Surfactant): Solubility Evaluation

| | Example # | | | | | |
|---|---|---|---|---|---|---|
| | A1 | A2* | A3* | A4* | A5 | A6 |
| Ammonyx ® Cetac 30, active % | 5.0 | 5.0 | 5.0 | 5.0 | 5.0 | 18.9 |
| C10-1, active % | 2.5 | | | | 5.0 | 18.9 |
| Alpha-Step ® PC-48, active % | | 2.5 | | | | |
| Stepanate ® SXS, active % | | | 2.5 | | | |
| Bio-Terge ® PAS-8S, active % | | | | 2.5 | | |
| Water | q.s. to 100 | q.s. to 100 | q.s. to 100 | q.s. to 100 | q.s. to 100 | q.s. to 100 |
| pH | 3.55 | 4.82 | 3.26 | 3.11 | — | — |
| Total actives (%) | 7.5 | 7.5 | 7.5 | 7.5 | 10.0 | 37.8 |
| Cat/an actives ratio | 5/2.5 | 5/2.5 | 5/2.5 | 5/2.5 | 5/5 | 1/1 |
| Cat/an molar ratio | 1.84 | 2.11 | 1.30 | 1.51 | 0.92 | 0.92 |
| Appearance | clear, low viscosity | cloudy, low viscosity | clear, viscoelastic | cloudy, viscous | clear, low viscosity | clear, low viscosity |
| Foam Volumes, mL | | | | | | |
| Initial | 340 | 320 | 150 | 140 | — | — |
| 5 min | 310 | 300 | 150 | 140 | — | — |
| Initial (+oil) | 175 | 145 | 115 | 115 | — | — |
| 5 min (+oil) | 175 | 145 | 115 | 115 | — | — |
| Sliming observed? | N | Y | N | Y | — | — |

*Comparative examples

As shown in Table 10, combination of a metathesis-based anionic surfactant, C10-1, with a cationic surfactant (Ammonyx® Cetac 30) provides clear, low-viscosity liquids. This contrasts with traditional anionic surfactants such as Bio-Terge® PAS-8S or Alpha-Step® PC-48, which often form a precipitate when combined with cationic surfactants. Stepanate® SXS acts as a counterion with Ammonyx® Cetac 30, giving a visoelastic liquid (Comparative Example A3), but that behavior is not seen with C10-1, where the mixture remains non-viscous.

The samples are further evaluated in a foaming test, with the C10-1/Cetac combination giving the best foaming, particularly with added oil. The C10-1/Cetac blend also gives a reduced level of oiling out or "sliming" upon dilution to 0.2 wt. % actives in preparation for the foam test.

Table 11 (below) shows a similar favorable solubility result when combining metathesis-derived anionic surfactant C12-1 with Ammonyx® Cetac 30.

TABLE 11

Metathesis-based Anionic Surfactant (C12-1) +
Ammonyx ® Cetac 30 (Cationic Surfactant): Solubility Evaluation

| | Example # | |
|---|---|---|
| | B1 | B2 |
| C12-1, active % | 5.0 | 10.0 |
| Ammonyx ® Cetac 30, active % | 5.0 | 2.0 |
| Water | q.s. to 100 | q.s. to 100 |
| Total actives (%) | 10 | 12 |
| C12-1/Cetac 30 actives ratio | 5/5 | 10/2 |
| C12-1/Cetac 30 molar ratio | 1/1 | 5/1 |
| Appearance, neat | clear | clear |
| Appearance, 0.2% actives | clear | hazy |

Tables 12-14 illustrate the solubility performance of blends made from a metathesis-based cationic surfactant and a variety of anionic surfactants. The metathesis-based cationic surfactants tested include an esteramine quat (C10-7, Table 12), an imidazoline quat (C10-13, Table 13), and a fatty amine benzyl quat (C10-40, Table 14). As shown in show acceptable compatibility when diluted to 0.2% actives (see Table 13). As shown in Table 14, blends of metathesis-based benzyl quat C10-40 with commercial or metathesis-based anionic surfactants provide good solubility at 0.2% actives.

TABLE 12

Blend of Metathesis-based Cationic (C10-7) and
Anionic Surfactants (C10-29) Synerqy and Solubility Evaluation

| | Active % | Moles |
|---|---|---|
| C10-7 (C10 DMEA Esterquat) | 31.9 | 0.00274 |
| C10-29 (C10 eFAME sulfonate) | 29.0 | 0.00275 |
| Blend total active %, neat | 60.9 | |
| Appearance, neat | clear, low viscosity | |

| | CMC (mg/L) | CMC (mol/L) | Surface tension at CMC (mN/m) |
|---|---|---|---|
| C10-7/C10-29 equimolar blend | 670 | $1.91 \times 10^{-3}$ | 34.8 |
| C10-7 | 342.6 | $9.32 \times 10^{-4}$ | 41.1 |
| C10-29 | 2244 | $6.75 \times 10^{-3}$ | 34.6 |
| Beta, calculated | | −5.62 | |

CMC = critical micelle concentration

TABLE 13

Blend of Metathesis-based Cationic Surfactant (C10-13) +
Anionic Surfactant: Solubility Evaluation

| | Active % |
|---|---|
| C10-13 (C10 DETA Quat) | 22.0 |
| Stepanol ® WA-Extra SLS | 22.0 |
| Blend total active %, neat | 44.0 |
| Appearance, neat | flowable paste |
| Appearance, 0.2% actives | hazy, homogeneous liquid |

TABLE 14

Metathesis-based Cationic Surfactant (C10-40) +
Anionic Surfactants: Solubility Evaluation

| | Example # | | | |
|---|---|---|---|---|
| | D1 | D2 | D3 | D4 |
| C10-40 (C10 Benzyl Quat), active % | 6.70 | 8.77 | 8.31 | 8.94 |
| Stepanol ® WA-Extra SLS, active % | 26.8 | | | |
| Bio-Terge ® AS-40, active % | | 35.1 | | |
| Alpha-Step ® PC-48, active % | | | 33.3 | |
| C10-26 (C10 DMA sulfonate), active % | | | | 35.8 |
| C10-40/other surfactant (molar) | 0.25 | 0.25 | 0.25 | 0.25 |
| % Actives, total | 33.5 | 43.9 | 41.6 | 44.7 |
| Appearance, neat | opaque, viscous, gel | pearl-like viscous liquid | clear liquid, low viscosity | two phases |
| Appearance, 0.2% actives | clear liquid | clear liquid | clear liquid | clear liquid |

Table 12, blends of C10-7 with C10-29, a metathesis-based anionic surfactant, are synergistic (β=−5.62) and provide clear, low-viscosity liquids. Blends of C10-13 with the commercial anionic surfactant Stepanol® WA Extra SLS We also found that certain metathesis-based surfactants provide good solubilities when combined with either an anionic or cationic surfactant. For instance, Table 15 shows that a metathesis-based DMAPA quat sulfonate provides clear liquids when blended with a cationic surfactant (Stepanquat® 1010-80) or anionic surfactants (Stepanol® WA Extra SLS or BTC® 2125M). Similar good solubilities are obtained when metathesis-based C10-21, a DMAPA amine oxide sulfonate, is blended with the same commercial cationic or anionic surfactants (Table 16).

TABLE 15

Metathesis-based Surfactant (C10-19) + Anionic or Cationic Surfactants: Solubility Evaluation

| | Example # | | |
|---|---|---|---|
| | E1 | E2 | E3 |
| C10-19 (C10 DMAPA Quat Sulfonate), active % | 26.3 | 19.9 | 22.7 |
| Stepanquat ® 1010-80, active % | 19.6 | | |
| Stepanol ® WA-Extra SLS, active % | | 12.4 | |
| BTC ® 2125M, active % | | | 17.6 |
| molar ratio | 1:1 | 1:1 | 1:1 |
| % Actives, total | 45.9 | 32.3 | 40.3 |
| Appearance, neat | clear liquid | clear liquid | clear liquid |
| Appearance, 0.2% actives | clear liquid | clear liquid | clear liquid |

TABLE 16

Metathesis-based Surfactant (C10-21) + Anionic or Cationic Surfactants: Solubility Evaluation

| | Example # | | |
|---|---|---|---|
| | F1 | F2 | F3 |
| C10-21 (C10 DMAPA AO Sulfonate), active % | 30.3 | 24.5 | 20.5 |
| Stepanquat ® 1010-80, active % | 29.1 | | |
| BTC ® 2125M, active % | | 24.5 | |
| Stepanol ® WA-Extra SLS, active % | | | 16.5 |
| molar ratio | 1:1 | 1:1 | 1:1 |
| % Actives, total | 59.5 | 49.0 | 37.0 |
| Appearance, neat | hazy liquid | clear liquid | clear liquid |
| Appearance, 0.2% actives | hazy liquid | clear liquid | clear liquid |

The preceding examples are meant only as illustrations. The following claims define the invention.

We claim:

1. A surfactant blend comprising:
    (a) an anionic surfactant; and
    (b) a cationic surfactant comprising:
        (i) a quaternized fatty amine having the structure:

$R^2(R^3)N^+(R^1)R^4 \; X^-$

wherein $R^1$ is $—C_{10}H_{18}—R^5$ or $—C_{18}H_{34}—N^+(R^2)(R^3)R^4 \; X^-$; each of $R^2$ and $R^3$ is independently substituted or unsubstituted alkyl, aryl, alkenyl, oxyalkylene, or polyoxyalkylene; $R^4$ is $C_1$-$C_6$ alkyl; $X^-$ is a halide, bicarbonate, bisulfate, or alkyl sulfate; and $R^5$ is hydrogen or $C_1$-$C_7$ alkyl; or (ii) a quaternized fatty amidoamine having the structure:

$R^4(R^3)(R^2)N^+(CH_2)_n \; NH(CO)R^1 \; X^-$ wherein: $R^1$ is $—C_9H_{16}—R^5$ or $—C_{16}H_{30}—(CO)NH(CH_2)_nN^+(R^2)(R^3)R^4 \; X^{31}$ ; each of $R^2$ and $R^3$ is independently substituted or unsubstituted alkyl, aryl, alkenyl, oxyalkylene, or polyoxyalkylene; $R^4$ is $C_1$-$C_6$ alkyl; $X^-$ is a halide, bicarbonate, bisulfate, or alkyl sulfate; $R^5$ is hydrogen or $C_1$-$C_7$ alkyl; and n=2 to 8.

2. The surfactant blend of claim 1 wherein the anionic surfactant is selected from the group consisting of alkyl sulfates, alkyl ether sulfates, olefin sulfonates, α-sulfonated alkyl esters, α-sulfonated alkyl carboxylates, alkyl aryl sulfonates, sulfoacetates, sulfosuccinates, isethionates, taurates, alkane sulfonates, alkylphenol alkoxylate sulfates, and mixtures thereof.

3. The surfactant blend of claim 1 wherein the anionic surfactant is sodium lauryl sulfate.

4. The surfactant blend of claim 1 comprising from 0.2 to 5 moles of the cationic surfactant per mole of the anionic surfactant.

5. The surfactant blend of claim 1 wherein the cationic surfactant comprises a quaternized fatty amine, and $R^1$ is $—(CH_2)_8—CH=CHR^5$ or $—(CH_2)_8—CH=CH—(CH_2)_8—N^+(R^2)(R^3)R^4 \; X^-$.

6. The surfactant blend of claim 1 wherein the cationic surfactant is a quaternized fatty amine having a structure selected from the group consisting of:

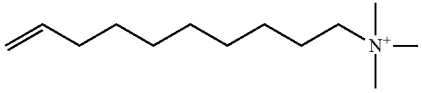

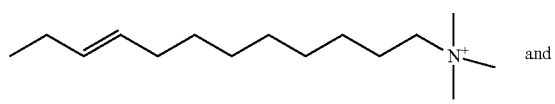

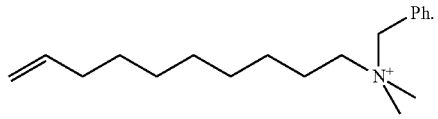

7. The surfactant blend of claim 1 wherein the cationic surfactant comprises a quaternized fatty amidoamine, and $R^1$ is $—(CH_2)_7—CH=CH—R^5$ or $—(CH_2)_7—CH=CH—(CH_2)_7—(CO)NH(CH_2)_nN^+(R^2)(R^3)R^4 \; X^-$.

8. The surfactant blend of claim 1 wherein the cationic surfactant is a quaternized fatty amidoamine having a structure selected from the group consisting of:

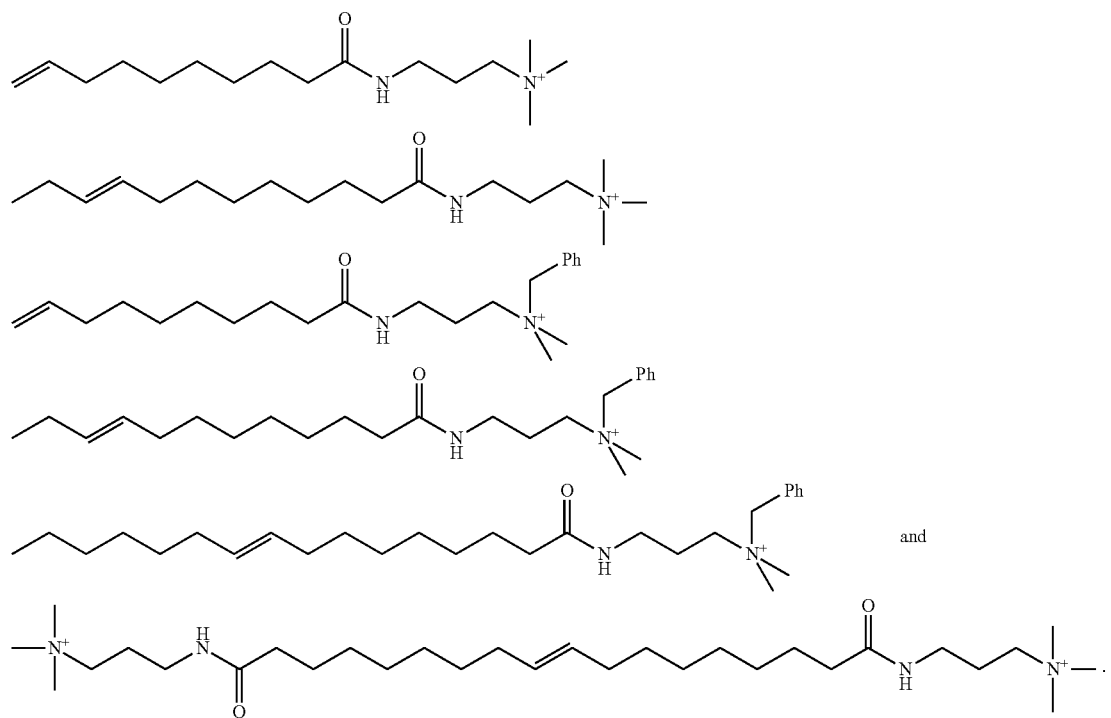
9. A surfactant blend comprising:
(a) an anionic surfactant; and
(b) a cationic surfactant comprising an imidazoline quat having a structure selected from the group consisting of:
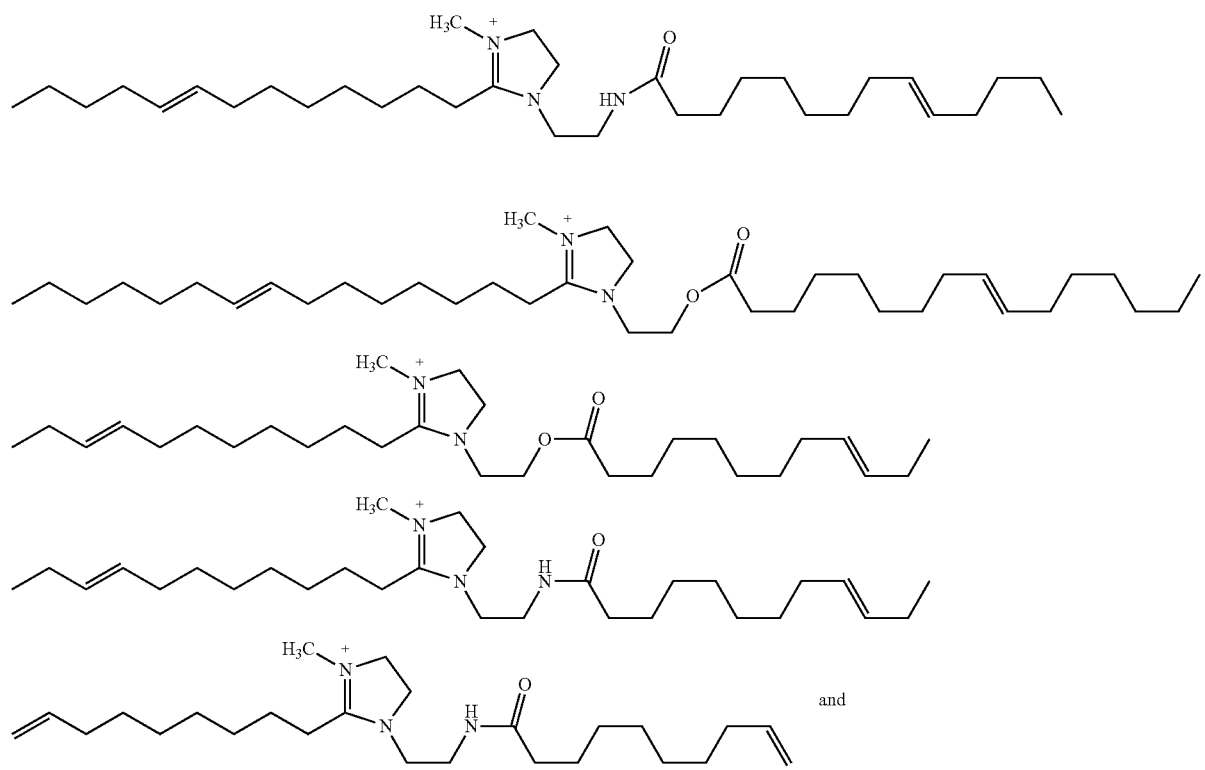

-continued

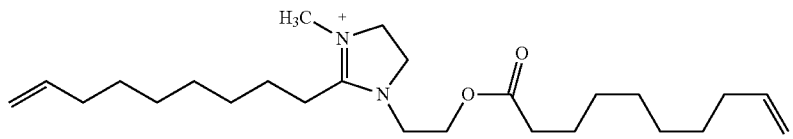

10. The surfactant blend of claim 9 wherein the anionic surfactant is selected from the group consisting of alkyl sulfates, alkyl ether sulfates, olefin sulfonates α-sulfonated alkyl esters, α-sulfonated alkyl carboxylates, alkyl aryl sulfonates, sulfoacetates, sulfosuccinates, isethionates, taurates, alkane sulfonates, alkylphenol alkoxylate sulfates, and mixtures thereof.

11. The surfactant blend of claim 9 wherein the anionic surfactant is sodium lauryl sulfate.

12. The surfactant blend of claim 9 comprising from 0.2 to 5 moles of the cationic surfactant per mole of the anionic surfactant.

13. A surfactant blend comprising:
(a) an anionic surfactant; and
(b) a cationic surfactant comprising an esteramine quat made by quaternizing an esteramine having the formula:

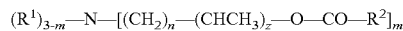

wherein:
$R^1$ is $C_1$-$C_6$ alkyl; $R^2$ is —$C_9H_{16}$—$R^3$ or —$C_{16}H_{30}$—$CO_2R^4$; $R^3$ is hydrogen or $C_1$-$C_7$ alkyl; $R^4$ is substituted or unsubstituted alkyl, aryl, alkenyl, oxyalkylene, polyoxyalkylene, glyceryl ester, or a mono- or divalent cation; m=1-3; n=1-4; z=0 or 1; and when z=0, n=2-4.

14. The surfactant blend of claim 13 wherein the anionic surfactant is selected from the group consisting of alkyl sulfates, alkyl ether sulfates, olefin sulfonates, α-sulfonated alkyl esters, α-sulfonated alkyl carboxylates, alkyl aryl sulfonates, sulfoacetates, sulfosuccinates, isethionates, taurates, alkane sulfonates, alkylphenol alkoxylate sulfates, and mixtures thereof.

15. The surfactant blend of claim 13 wherein the anionic surfactant is sodium lauryl sulfate.

16. The surfactant blend of claim 13 comprising from 0.2 to 5 moles of the cationic surfactant per mole of the anionic surfactant.

17. The esteramine quat of claim 13 wherein $R^2$ is —$(CH_2)_7$—CH=CH$R^3$ or —$(CH_2)_7$—CH=CH—$(CH_2)_7$—$CO_2R^4$.

18. The surfactant blend of claim 13 wherein the esteramine quat has a structure selected from the group consisting of:

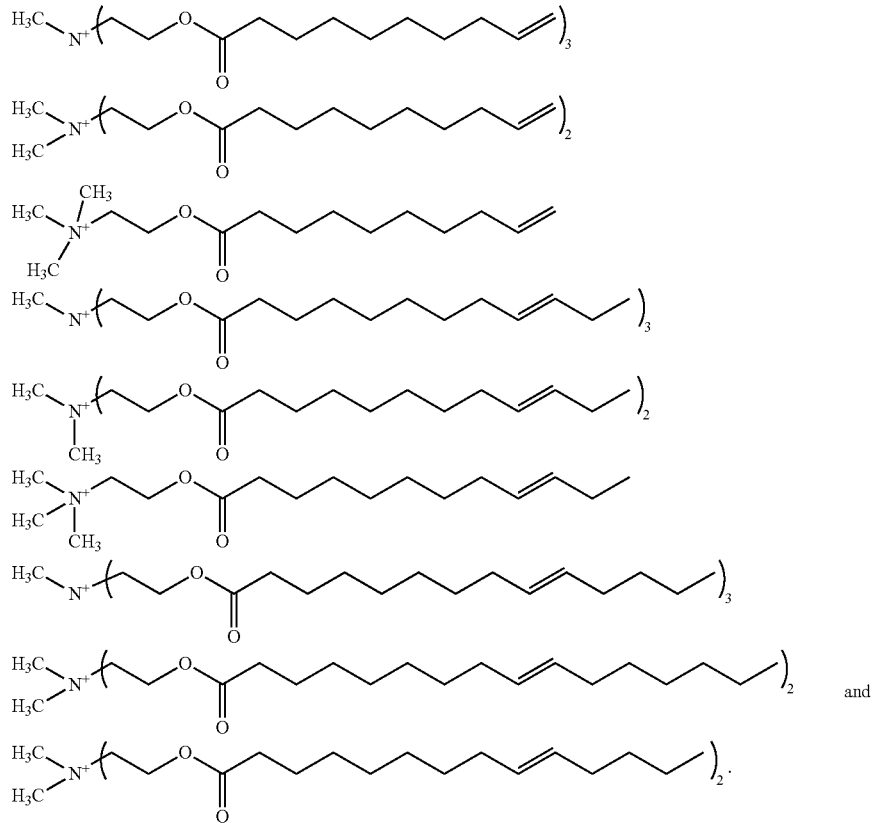

* * * * *